US012630797B2

(12) United States Patent
Roulston et al.

(10) Patent No.: US 12,630,797 B2
(45) Date of Patent: May 19, 2026

(54) APPARATUS, METHODS, AND SYSTEMS FOR MAINTAINING HEALTHY PLANKTON POPULATIONS

(71) Applicant: Industrial Plankton Inc., Victoria (CA)

(72) Inventors: Robert Roulston, Victoria (CA); Stuart De Haas, Victoria (CA); Wilson Hay, Victoria (CA)

(73) Assignee: INDUSTRIAL PLANKTON INC., Victoria (CA)

( * ) Notice: Subject to any disclaimer, the term of this patent is extended or adjusted under 35 U.S.C. 154(b) by 860 days.

(21) Appl. No.: 17/799,664

(22) PCT Filed: Feb. 13, 2021

(86) PCT No.: PCT/CA2021/050159
§ 371 (c)(1),
(2) Date: Aug. 13, 2022

(87) PCT Pub. No.: WO2021/159217
PCT Pub. Date: Aug. 19, 2021

(65) Prior Publication Data
US 2023/0075029 A1 Mar. 9, 2023

Related U.S. Application Data

(60) Provisional application No. 62/976,341, filed on Feb. 13, 2020.

(51) Int. Cl.
*C12M 1/00* (2006.01)
*C12M 3/04* (2006.01)
*C12N 1/10* (2006.01)

(52) U.S. Cl.
CPC ........... *C12M 27/12* (2013.01); *C12M 23/40* (2013.01); *C12M 29/04* (2013.01); *C12M 39/00* (2013.01); *C12N 1/10* (2013.01)

(58) Field of Classification Search
CPC ......... Y02A 40/81; C12M 21/02; A01G 33/00
See application file for complete search history.

(56) References Cited

U.S. PATENT DOCUMENTS

| | | | | |
|---|---|---|---|---|
| 4,218,322 A * | 8/1980 | Kojima | ................ | B01D 33/503 210/402 |
| 4,259,926 A * | 4/1981 | Marliave | ................ | A01K 61/20 47/1.4 |
| 5,647,983 A * | 7/1997 | Limcaco | ................ | C02F 3/082 210/150 |
| 9,688,950 B2 * | 6/2017 | Roulston | ................ | C12M 37/00 |

(Continued)

FOREIGN PATENT DOCUMENTS

JP 2005261343 A 9/2005

OTHER PUBLICATIONS

Banrie, "Phytoplankton Culture for Aquaculture Feed". The Fish Site, Feb. 9, 2013 (Sep. 2, 2013), [Website], [online] [retrieved on Aug. 11, 2022 (Nov. 8, 2022)]. Retrieved from the Internet: https://thefishsite.com/articles/phytoplankton-culture-for-aquaculture-feed.

(Continued)

*Primary Examiner* — Jonathan M Hurst

(57) ABSTRACT

One aspect of this disclosure is a method for maintaining a plankton population in a culture medium by removing particles from the culture medium. The method may comprise rotating a filter body to lift the particles from the culture medium with a filter of the filter body, positioning the filter relative to a conduit so that a first portion of the lifted particles fall into the conduit, directing a removal fluid toward the filter body to move a second portion of the lifted particles off the filter and into the conduit with impact forces applied by the removal fluid, and/or outputting an effluent flow from the conduit. The effluent flow may comprise the first and second portions of the lifted particles and a portion of the removal fluid. Aspects of related apparatus, methods, and systems also are disclosed.

20 Claims, 24 Drawing Sheets

(56) References Cited

U.S. PATENT DOCUMENTS

2012/0184001 A1*   7/2012   Stephen ................. A01K 61/60
                                                             426/417
2015/0264897 A1*   9/2015   Limcaco ............... A01K 61/00
                                                             119/224

OTHER PUBLICATIONS

Huang et al., "Ammonia-oxidizing bacteria and archaea within bio filters of a commercial recirculating marine aquaculture system". AMB Express, Oct. 2, 2018 (Feb. 10, 2018), vol. 8, Document 17, pp. 1-12, ISSN 2191-0855.

Kim et al., "A bubble-powered zooplankton grazing wheel". Journal of Plankton Research, 2003, vol. 25, No. 6, pp. 683-686, ISSN 0142-7873.

Van Der Meeren et al., "Copepod production in a saltwater pond system: a reliable method for achievement of natural prey in start-feeding of marine fish larvae". Aquaculture Engineering, 2014, vol. 62, pp. 17-27, ISSN 0144-8609.

Vijverberg, "Culture techniques for studies on the growth, development and reproduction of copepods and cladocerans under laboratory and in situ conditions: a review". Freshwater Biology, 1989, vol. 2, pp. 317-373, ISSN 1365-2427.

International Preliminary Report on Patentability for International Patent Application No. PCT/CA2021/050159 mailed May 27, 2022 (38 pages).

International Search Report and Written Opinion for International Patent Application No. PCT/CA2021/050159 mailed Apr. 19, 2021 (11 pages) (submitted together with an interim copy of WO2021/159217).

* cited by examiner

263

268B

268P

271

265

263

264

265

268

272

268B

268P

Figure 23:
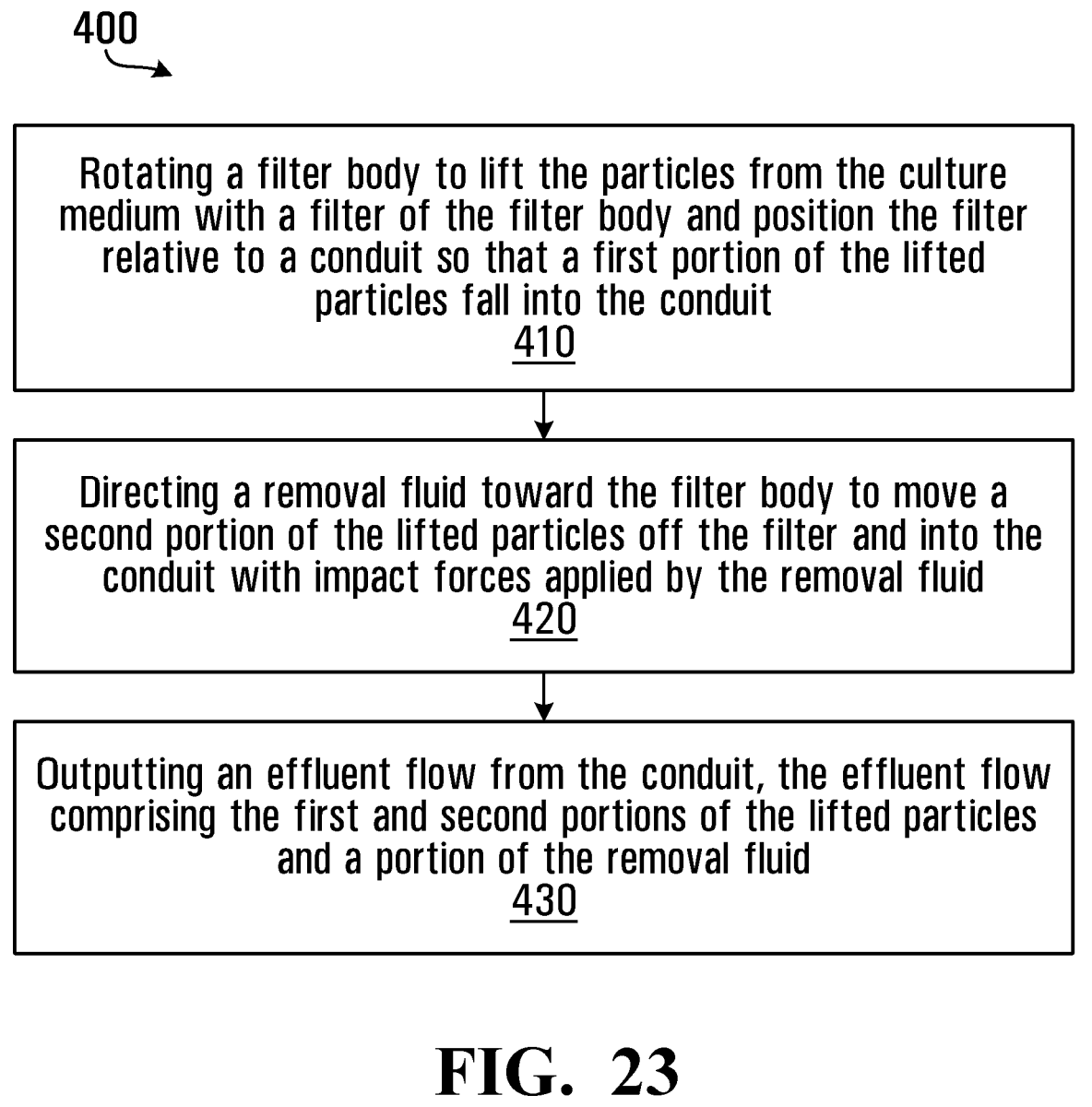

400

Rotating a filter body to lift the particles from the culture medium with a filter of the filter body and position the filter relative to a conduit so that a first portion of the lifted particles fall into the conduit
410

Directing a removal fluid toward the filter body to move a second portion of the lifted particles off the filter and into the conduit with impact forces applied by the removal fluid
420

Outputting an effluent flow from the conduit, the effluent flow comprising the first and second portions of the lifted particles and a portion of the removal fluid
430

Figure 24:
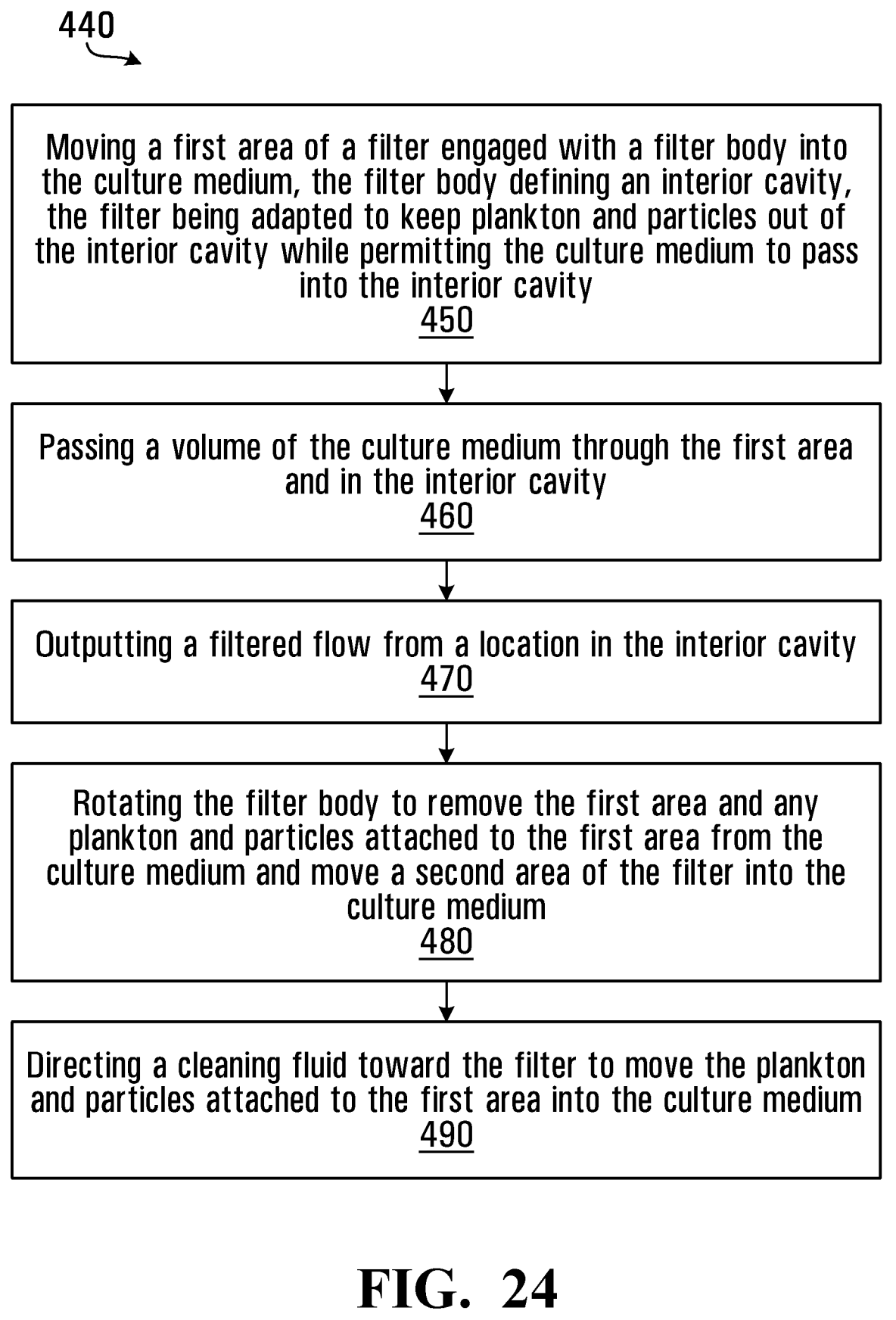

Moving a first area of a filter engaged with a filter body into
the culture medium, the filter body defining an interior cavity,
the filter being adapted to keep plankton and particles out of
the interior cavity while permitting the culture medium to pass
into the interior cavity
450

Passing a volume of the culture medium through the first area
and in the interior cavity
460

Outputting a filtered flow from a location in the interior cavity
470

Rotating the filter body to remove the first area and any
plankton and particles attached to the first area from the
culture medium and move a second area of the filter into the
culture medium
480

Directing a cleaning fluid toward the filter to move the plankton
and particles attached to the first area into the culture medium
490

APPARATUS, METHODS, AND SYSTEMS FOR MAINTAINING HEALTHY PLANKTON POPULATIONS

CROSS-REFERENCE TO RELATED APPLICATIONS

This application is a § 371 National Stage Entry of International Patent Application No. PCT/CA2021/050159, filed Feb. 13, 2021, claiming the benefit of priority of U.S. Provisional Patent Application No. 62/976,341, filed Feb. 13, 2020, the entireties of which are incorporated by reference into this application.

BACKGROUND

Field

This disclosure relates generally to maintaining healthy plankton populations. Particular aspects relate to apparatus, methods, and systems for maintaining healthy plankton populations.

Description of Related Art

Plankton comprises many small and microscopic organisms drifting or floating in salt or fresh water, including rotifers and copepods, which actively swim around their environment eating phytoplankton. Rotifers may be an important food source for many larval fish species, such as sablefish, sea bream and mullet. For example, many of these larval fish hatch with mouths that are too small to eat larger prey and yet will only eat food that is actively swimming, making rotifers a viable food source.

In nature, rotifers are typically found at lower concentrations limited by the amount of food available. When growing rotifers for use in aquaculture, higher concentrations may be achieved by containing a population of rotifers in a tank and providing the contained population with a steady supply of food. Waste accumulation and removal is a known problem associated with higher concentrations of rotifers. For example, if unchecked, dissolved wastes (e.g., such as ammonium) and/or particulate wastes (e.g., such as uneaten food) can accumulate in the tank, potentially killing some of the rotifers directly through toxicity or indirectly by consuming too much of the oxygen in the tank.

SUMMARY

One aspect of this disclosure is a method for maintaining a plankton population in a culture medium by removing particles from the culture medium. The method may comprise rotating a filter body to lift the particles from the culture medium with a filter of the filter body, positioning the filter relative to a conduit so that a first portion of the lifted particles fall into the conduit, and directing a removal fluid toward the filter body to move a second portion of the lifted particles off the filter and into the conduit with impact forces applied by the removal fluid. The method also may comprise outputting an effluent flow from the conduit. The effluent flow may comprise the first and second portions of the lifted particles and a portion of the removal fluid.

Rotating the filter body to lift the particles from the culture medium may comprise rotating the filter into a lift position where a lift surface of the filter may be generally parallel with a top surface of the culture medium. Rotating the filter body to position the filter relative to the conduit may comprise rotating the lift surface from the lift position to a dump position where the lift surface may be generally perpendicular with the top surface of the culture medium. The method may comprise rotating the filter body from the dump position to a removal position where the lift surface may be inverted over the conduit so that a back of the lift surface intersects a flow path of the removal fluid. Directing the removal fluid may comprise directing the removal fluid along the flow path so that the impact forces may be applied to the back of the lift surface to push the second portion of the lifted particles away from the lift surface and into the conduit.

The filter body may comprise a plurality of filters, and the method may involve repeating the rotating, directing, and outputting steps for each filter of the plurality of filters. The culture medium may be stored in a tank, the filter body may be rotatable in a frame, and the method may comprise mounting the frame to the tank so that only a lower portion of the filter body and the plurality of filters may be submerged in the culture medium at a time to limit biofouling of the filter body and the plurality of filters. The method may comprise one or both of: removing the filter body from the frame and removing the filter from the filter body.

Another aspect of this disclosure is a method for maintaining a plankton population in a culture medium by filtering the culture medium. The method may comprise moving a first area of a filter engaged with a filter body into the culture medium, the filter body defining an interior cavity, the filter being adapted to keep plankton and particles out of the interior cavity while permitting the culture medium to pass into the interior cavity, passing a volume of the culture medium through the first area and in the interior cavity, and outputting a filtered flow from a location in the interior cavity. The method may comprise rotating the filter body to remove the first area and any plankton and particles attached to the first area from the culture medium, moving a second area of the filter into the culture medium, and directing a cleaning fluid toward the filter to move the plankton and particles attached to the first area into the culture medium.

The method may comprise rotating the filter body to remove the second area and any plankton and particles attached to the second area from the culture medium and move a different area of the filter into the culture medium. The method may comprise repeating the directing step with the second area. The method may comprise continuously outputting the filtered flow while intermittently repeating the passing, rotating, and directing steps for each different area of the filter. The method may comprise performing the directing step while performing the rotating step. The directing step may involve one or both of: directing a first amount of the cleaning fluid toward an interior surface of the first area from a location in the interior cavity and directing a second amount of the cleaning fluid toward an exterior surface of the first area from a location outside the interior cavity.

The filter may comprise openings sized to keep the plankton and particles out of the interior cavity while permitting the culture medium to pass into the interior cavity and a portion of the plankton and particles attached to the first area may be engaged with the openings and exterior surfaces of the first area. The method may comprise directing the cleaning fluid toward an interior surface of the first area, from a location in the interior cavity, to disengage the portion of the plankton and particles from the openings and the exterior surfaces of the first area. The culture medium may be stored in a tank, the filter body may be rotatable in a frame, and the method may comprise mounting the frame to the tank so that only one different area of the filter is submerged in the culture medium at a time to limit biofouling of the filter and the filter body. The method may comprise one or both of: removing the filter body from the frame and removing the filter from the filter body.

Rotating the filter body to lift the particles may comprise scooping the particles from the culture medium with the filter. Rotating the filter body to lift the particles may comprise lifting the filter out of the culture medium. Lifting the filter out of the culture medium may comprise moving the filter in a generally linear direction from a submerged position in the culture medium to a lifted position outside of the culture medium. The generally linear direction may be generally vertical. Rotating the filter body to position the filter comprises rotating the filter from a lift position where the filter is generally perpendicular with a top surface of the culture medium to a dump position where the filter is generally parallel with the top surface of the culture medium. Rotating the filter body to position the filter may comprise moving the filter body across an edge of the conduit and positioning the filter over the conduit so that the first portion of the lifted particles fall into the conduit. Directing the removal fluid toward the filter body may occur when the filter is positioned over the conduit to move the second portion of the lifted particles into the conduit through openings of the filter with the impact forces. The filter may comprise at least two materials and directing the removal fluid toward the filter body occurs when the filter is positioned over the conduit to move the second portion of the lifted particles into the conduit through openings of the at least two materials with the impact forces. The filter may comprise a pocket and directing the removal fluid toward the filter body may occur when the pocket is positioned over the conduit to move the second portion of the lifted particles into the conduit through openings of the pocket with the impact forces. The filter body may comprise a plurality of filters, each filter may comprise a pocket, and the method may comprise repeating the rotating, directing, and outputting steps for each pocket.

Another aspect of the present disclosure is a method for maintaining a plankton population in a culture medium contained in a culture tank. The method may comprise removing particles from the culture medium in the culture tank, outputting a filtered flow from a filtered portion of the culture medium in the culture tank, and converting the filtered flow in to a processed flow by removing toxins from the filtered flow and adding oxygen to the filtered flow. The method also may comprise inputting the processed flow to the culture medium in the culture tank.

Removing the toxins may comprise one or more of: exposing the filtered flow to UV-light, modifying a temperature of the filtered flow, removing organic waste from the filtered flow, converting ammonia in the filtered flow to nitrates, and adding a supplement to the filtered flow. Removing the toxins may comprise exposing the filtered flow to a UV-light prior to adding the oxygen. Adding oxygen may comprise performing an oxygenation process, which may comprise pressurizing the filtered flow, adding oxygen to the pressurized filtered flow, and/or dissolving the oxygen into the filtered flow. The method may comprise continuously performing the oxygenation process while intermittently removing particles from the culture medium in the culture tank.

The method may comprise determining a quality of the culture medium in the culture tank and intermittently removing particles from the culture medium in the culture tank responsive to the quality of the culture medium. The method may comprise maintaining a stored volume of the culture medium by inputting the filtered flow to a buffer tank prior to adding the oxygen and performing an oxygenation process with a first flow from the stored volume in the buffer tank. Inputting the processed flow may comprise inputting the first flow to the culture medium in the culture tank after performing the oxygenation process. Removing toxins from the filtered flow may comprise removing the organic waste and the nitrates from the stored volume in the buffer tank. Removing the organic waste and the nitrates from the stored volume in the buffer tank may comprise performing a cleaning process.

The cleaning process may comprise outputting a second flow from the stored volume in the buffer tank, removing the organic waste from the second flow, converting ammonia in the second flow to nitrates, and inputting the second flow to the stored volume in the buffer tank after removing the organic waste and converting the ammonia. Removing the organic waste may comprise pressurizing the second flow and passing the pressurized flow through a water column. Converting the ammonia may comprise exposing the second flow to nitrifying bacteria, converting the ammonia to nitrites with the nitrifying bacteria, and converting the nitrites to nitrates with the nitrifying bacteria. Exposing the second flow to the nitrifying bacteria may comprise generating an additional stored volume of the culture medium by outputting the second flow to a biofilter tank after removing the organic waste and exposing the additional stored volume to a population of nitrifying bacteria contained in the biofilter tank. The method may comprise outputting a third flow from the additional stored volume in the biofilter tank to the stored volume in the buffer tank. The method may comprise modifying a temperature of the additional stored volume in the biofilter tank.

Performing a feeding process may comprise performing the oxygenation process with the first flow from the stored volume without inputting the second flow to the stored volume and continuously outputting a fourth flow from the additional stored volume to the cleaning process in order to remove additional organic waste from and convert additional ammonia in the additional stored volume. Removing the particles may comprise rotating a first filter body to lift the particles from the culture medium with a filter of the first filter body, positioning the filter relative to a conduit so that a first portion of the lifted particles fall into the conduit, and directing a removal fluid toward the first filter body to move a second portion of the lifted particles off the filter and into the conduit with impact forces applied by the removal fluid and outputting an effluent flow from the conduit. The effluent flow may comprise the first and second portions of the lifted particles and a portion of the removal fluid.

Outputting the filtered flow may comprise moving a first area of a second filter engaged with a second filter body into the culture medium, the second filter body defining an interior cavity, the second filter being adapted to keep plankton and particles out of the interior cavity while permitting the culture medium to pass into the interior cavity, generating the filtered portion of the culture medium by passing a volume of the culture medium through the first area and in the interior cavity, and outputting the filtered flow from a location in the interior cavity. Outputting the filtered flow may comprise rotating the filter body to remove the first area of the filter and any plankton and particles attached to the first area from the culture medium and moving a second area of the filter into the culture medium. Outputting the filtered flow may comprise directing a cleaning fluid toward the filter to move the plankton and particles attached to the first area into the culture medium.

The method may comprise outputting, from a controller, first control signals causing the rotating and directing steps associated with removing the particles to be performed at first intervals and outputting, from the controller, second control signals causing the rotating and directing steps associated with filtering the culture medium to be performed at second intervals. The first intervals may be independent of the second intervals. The method may comprise receiving, with the controller, control data associated with a quality metric of the culture medium from one or more sensors in data communication with the controller and generating, with the controller, the first and second control signals so as to maintain or modify the quality metric responsive to the control data.

Another aspect of the present disclosure is an apparatus for maintaining a plankton population in a culture medium by removing particles from the culture medium. The apparatus may comprise a drive element adapted to rotate a filter body to lift the particles from the culture medium with a filter of the filter body and position the filter relative to a conduit so that a first portion of the lifted particles fall into the conduit. The apparatus may comprise one or more nozzles adapted to direct a removal fluid toward the filter body to move a second portion of the lifted particles off the filter and into the conduit with impact forces applied by the removal fluid. The conduit may be adapted to output an effluent flow comprising the first and second portions of the lifted particles and a portion of the removal fluid.

The drive element may be adapted to rotate the filter body to lift the particles from the culture medium by rotating the filter into a lift position where a lift surface of the filter may be generally parallel with a top surface of the culture medium. The drive element may be adapted to rotate the filter body to position the filter relative to the conduit by rotating the lift surface from the lift position to a dump position where the lift surface may be generally perpendicular with the top surface of the culture medium. The drive element may be adapted to rotate the filter body from the dump position to a removal position where the lift surface may be inverted over the conduit so that a back of the lift surface intersects a flow path of the removal fluid, and the one or more nozzles may be adapted to direct the removal fluid along the flow path so that the impact forces are applied to the back of the lift surface to push the second portion of the lifted particles away from the lift surface and into the conduit. The filter body may comprise a plurality of filters.

The culture medium may be stored in a tank, the filter body may be rotatable in a frame, and the frame may be engageable with the tank so that only a lower portion of the filter body and the plurality of filters may be submerged in the culture medium at a time to limit biofouling of the filter body and the plurality of filters. The apparatus may comprise at least one of: the first filter body may be removable from the frame and the filter may be removable from the filter body.

The drive element may be adapted to rotate the filter body to scoop the particles from the culture medium with the filter. The drive element may be adapted to lift the filter out of the culture medium. The drive element may be adapted to move the filter in a generally linear direction from a submerged position in the culture medium to a lifted position outside of the culture medium. The generally linear direction may be generally vertical. The drive element may be adapted to rotate the filter body from a lift position where the filter is generally perpendicular with a top surface of the culture medium to a dump position where the filter is generally parallel with the top surface of the culture medium. The drive element may be adapted to rotate the filter body to move the filter body across an edge of the conduit and position the filter over the conduit so that the first portion of the lifted particles fall into the conduit. The one or more nozzles may be adapted to direct the removal fluid toward the filter body when the filter is positioned over the conduit to move the second portion of the lifted particles into the conduit through openings of the filter with the impact forces. The filter may comprise at least two materials and the one or more nozzles may be adapted to direct the removal fluid toward the filter body when the filter is positioned over the conduit to move the second portion of the lifted particles into the conduit through openings of each material of the at least two materials with the impact forces. The filter may comprise a pocket and directing the removal fluid toward the filter body may comprise moving the second portion of the lifted particles into the conduit through the pocket. The filter body may comprise a plurality of filters and each filter may comprise a pocket. The filter may comprise of a plurality of porous layers. The filter may comprise a resiliently deformable mesh structure defining a pocket. The filter body may comprise a belt. The filter may comprise a plurality of filters and each filter of the plurality of filters may comprise a pocket extending outwardly from the belt. The belt may comprise a first layer engageable with the drive element and a second layer comprising the plurality of filters.

Another aspect of the present disclosure is an apparatus for maintaining a plankton population in a culture medium by filtering the culture medium. The apparatus may comprise a filter body defining an interior cavity, a filter engaged with the filter body and adapted to keep plankton and particles out of the interior cavity while permitting a volume of the culture medium to pass into the interior cavity through a first area of the filter, and an outlet adapted to output a filtered flow from a location in the interior cavity. The apparatus may comprise a drive element adapted to rotate the filter body to remove the first area of the filter and any plankton and particles attached to the first area from the culture medium and move a second area of the filter into the culture medium. The apparatus may comprise one or more nozzles adapted to direct a cleaning fluid toward the filter body to move the plankton and particles attached to the first area into the culture medium.

The drive element may be adapted to rotate the filter body to remove the second area of the filter and any plankton and particles attached to the second area from the culture medium and move a different area of the filter into the culture medium. The one or more nozzles may be adapted to direct the cleaning fluid toward the filter body to move the plankton and particles attached to the second area into the culture medium. The drive element may be adapted to intermittently rotate the filter body and the outlet may be adapted to continuously output the filtered flow when the drive element may be rotating the filter body. The one or more nozzles may be adapted to direct the cleaning fluid when the drive element may be rotating the filter body. The one or more nozzles may be adapted to direct one or both of a first amount of the cleaning fluid toward an interior surface of the first area from a location in the interior cavity and a second amount of the cleaning fluid toward an exterior of the first area from a location outside the interior cavity.

The filter may comprise openings sized to keep the plankton and particles out of the interior cavity while permitting the culture medium to pass into the interior cavity, a portion of the plankton and particles attached to the first area may be engaged with the openings and exterior surfaces of the first area, and the one or more nozzles may be adapted to direct the cleaning fluid toward an interior surface of the first area, from a location in the interior cavity, to disengage the portion of the plankton and particles attached to the first area from the openings and the exterior surfaces of the first area. The culture medium may be stored in a tank, the filter body may be rotatable in a frame, and frame may be engageable with the tank so that only one different area of the filter is submerged in the culture medium at a time to limit biofouling of the filter and the filter body. The filter body may be removable from the frame and/or the filter may be removable from the filter body.

Another aspect of the present disclosure is a system for maintaining a plankton population in a culture medium contained in a culture tank. The system may comprise a first apparatus adapted to remove particles from the culture medium in the culture tank, a second apparatus adapted to output a filtered flow from a filtered portion of the culture medium in the culture tank, and a treatment system operable to convert the filtered flow. The treatment system may comprise an oxygenation loop operable to add oxygen to the filtered flow and/or a treatment loop operable to remove toxins from the filtered flow.

The treatment loop may be adapted to expose the filtered flow to UV-light, modify a temperature of the filtered flow, remove organic waste from the filtered flow, convert ammonia in the filtered flow to nitrates, and add a supplement to the filtered flow. The treatment loop may comprise a UV filter adapted to remove the toxins by exposing the filtered flow to a UV-light. The oxygenation loop may be adapted to pressurize the filtered flow, add oxygen to the pressurized filtered flow, and dissolve the oxygen into the filtered flow. The oxygenation loop may be operable continuously while the treatment loop may be operable intermittently.

The first apparatus may be adapted to determine a quality of the culture medium in the culture tank and intermittently remove particles from the culture medium in the culture tank responsive to the quality of the culture medium. The treatment system may be adapted to maintain a stored volume of the culture medium by inputting the filtered flow to a buffer tank, directing a first flow from the stored volume into the oxygenation loop, and inputting the first flow to the culture medium in the culture tank after circulating it through the oxygenation loop. The treatment loop may be adapted to remove the organic waste and the nitrates from the stored volume in the buffer tank. The treatment loop may be adapted to output a second flow from the stored volume in the buffer tank, remove the organic waste from the second flow, convert ammonia in the second flow to nitrates, and input the second flow to the stored volume in the buffer tank after removing the organic waste and converting the ammonia.

The treatment loop may comprise a pump adapted to pressurize the second flow and a protein skimmer adapted to remove the organic waste. The treatment loop may comprise a biofilter tank adapted to expose the second flow to nitrifying bacteria, convert the ammonia to nitrites with the nitrifying bacteria, and convert the nitrites to nitrates with the nitrifying bacteria. The biofilter tank may contain a population of nitrifying bacteria and be adapted to generate an additional stored volume of the culture medium by inputting the second flow after removing the organic waste and exposing the additional stored volume to the population of nitrifying bacteria. The treatment loop may be adapted to output a third flow from the additional stored volume in the biofilter tank to the stored volume in the buffer tank. The biofilter tank may be adapted to modify a temperature of the additional stored volume. The treatment system may be adapted to input the first flow from the stored volume to the oxygenation loop without inputting the second flow to the stored volume to the treatment loop and continuously output a fourth flow to the biofilter tank in order to remove additional organic waste from and convert additional ammonia in the additional stored volume.

The first apparatus may comprise a first drive element adapted to rotate a first filter body to lift the particles from the culture medium with a filter of the first filter body, and position the filter relative to a conduit so that a first portion of the lifted particles fall into the conduit and one or more first nozzles adapted to direct a removal fluid toward the first filter body to move a second portion of the lifted particles off the filter and into the conduit with impact forces applied by the removal fluid. The conduit may be adapted to output an effluent flow comprising the first and second portions of the lifted particles and a portion of the removal fluid.

The second apparatus may comprise a second filter body defining an interior cavity, a second filter engaged with the second filter body to keep plankton and particles out of the interior cavity while permitting a volume of the culture medium to pass into the interior cavity, an outlet adapted to output a filtered flow from a location in the interior cavity, and a second drive element adapted to rotate the second filter body to remove a first area of the second filter and any plankton and particles attached to the first area from the culture medium, and move a second area of the second filter into the culture medium. The second apparatus may further include one or more second nozzles adapted to direct a cleaning fluid toward the second filter body to move the plankton and particles attached to the first area into the culture medium.

The conduit may be adapted to output the effluent flow into a disposal system, the outlet may be adapted to output the filtered flow into a treatment system, and the treatment system may be adapted to convert the filtered flow into an additional volume of the culture medium by removing toxins and adding nutrients and return a processed flow of the additional volume to the culture medium. The treatment system may comprise one or more of: a UV filter, a chiller, a heater, a protein skimmer, a biofilter tank, an oxygen pump, and an oxygen cone.

The system may comprise a controller adapted to output first control signals for operating the first drive element and the one or more first nozzles at first intervals and output second control signals for operating the second drive element and the one or more second nozzles at second intervals. The first intervals may be independent of the second intervals. The system may comprise one or more sensors in data communication with the controller and adapted to output control data associated with a quality metric of the culture medium. The controller may be adapted to generate the first and second control signals so as to maintain or modify the quality metric responsive to the control data. The one or more sensors may comprise an optical sensor adapted to determine the quality metric.

Another aspect of this disclosure is a system for maintaining a plankton population in a culture medium contained in a culture tank. The system may comprise: a first apparatus adapted to remove particles from the culture medium in the culture tank; a second apparatus adapted to output a filtered flow from a filtered portion of the culture medium in the culture tank; a treatment system operable to convert the filtered flow into a treated culture medium, the treatment system comprising: a first loop operable to add food to the culture tank; and a second loop operable to add the treated culture medium into culture tank.

The system may comprise one or more sources operable to continuously add air and oxygen to the culture medium in the culture tank. The system may comprise a diffuser operable to diffuse the air and oxygen in a first direction toward the second apparatus that causes particles in the culture medium to move in a second direction toward the first apparatus. The treatment system may comprise a treatment loop operable to remove toxins from the filtered flow. Treatment loop may be operable continuously and the first and second loops may be operable intermittently.

BRIEF DESCRIPTION OF THE DRAWINGS

The accompanying drawings, which are incorporated in and constitute part of this disclosure, illustrate exemplary aspects that, together with the written descriptions, serve to explain the principles of this disclosure. Numerous aspects are particularly described, pointed out, and taught in the written descriptions. Some structural and operational aspects may be even better understood by referencing the written portions together with the accompanying drawings, of which:

FIG. 23 depicts an exemplary method for maintaining healthy plankton populations.

FIG. 24 depicts an exemplary method for maintaining healthy plankton populations.

DETAILED DESCRIPTION

Figure 1:
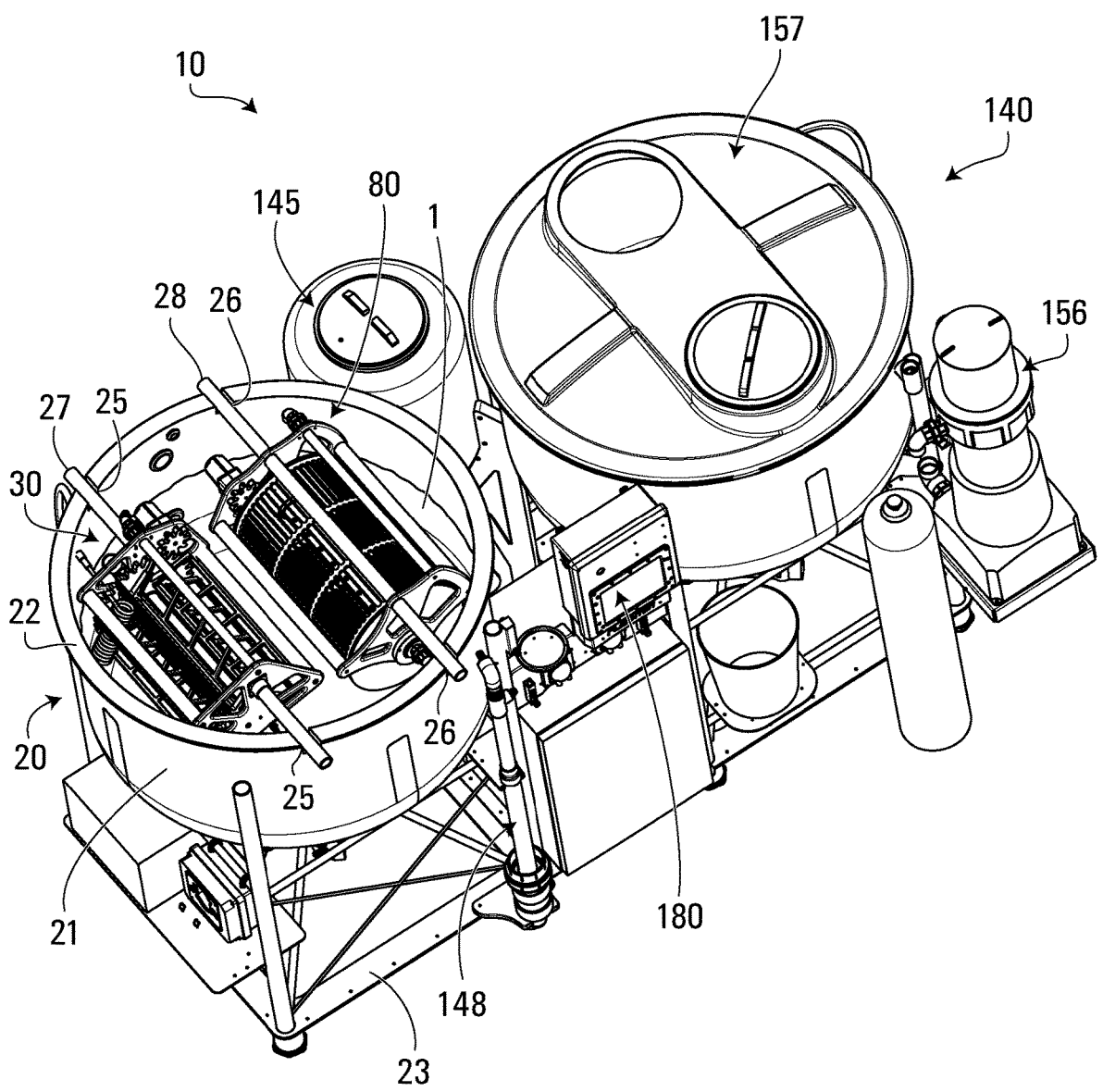
FIG. 1 depicts a perspective view of an exemplary system for maintaining healthy plankton populations.

Aspects of the present disclosure are not limited to the exemplary structural details and component arrangements described in this description and shown in the accompanying drawings. Many aspects of this disclosure may be applicable to other aspects and/or capable of being practiced or carried out in various variants of use, including the examples described herein.

Throughout the written descriptions, specific details are set forth in order to provide a more thorough understanding to persons of ordinary skill in the art. For convenience and ease of description, some well-known elements may be described conceptually to avoid unnecessarily obscuring the focus of this disclosure. In this regard, the written descriptions and accompanying drawings should be interpreted as illustrative rather than restrictive, enabling rather than limiting.

Exemplary aspects of this disclosure reference various apparatus, methods, and systems for maintaining healthy plankton populations. Some aspects are described with reference to maintaining particular type of plankton (e.g., rotifers) utilizing particular mechanical components (e.g., tanks, filters, pumps, etc.) to perform a particular function (e.g., removing waste from the tanks). Unless claimed, these descriptions are provided for convenience and not intended to limit this disclosure. Accordingly, any aspects described in this disclosure may be utilized with any similar apparatus, methods, and/or systems.

Several reference axes are described, including a filter axis X1-X1 and a filter axis X2-X2. Various aspects are described relative to these axes. For example, various elements may be aligned with and/or rotatable about axes X1-X1 or X2-X2. Other axes may be non-parallel with these axes, meaning that they extend across and/or intersect these axes. For example, at least two other axes may be arranged orthogonally with axis X1-X1 or X2-X2 to define a Cartesian coordinate system. Additional reference axes, movements, and forces may be similarly described. These relative terms are provided for convenience and do not limit this disclosure unless claimed.

Inclusive terms such as "comprises," "comprising," "includes," "including," and variations thereof, are intended to cover a non-exclusive inclusion, such that any apparatus, method, system, or element thereof comprising a list of elements does not include only those elements, but may include other elements not expressly listed and/or inherent thereto. Unless stated otherwise, the term "exemplary" is used in the sense of "example," rather than "ideal." Various terms of approximation may be used in this disclosure, including "approximately" and "generally." Approximately means "roughly" or within 10% of a stated number or outcome. Generally means "usually" or more than a 50% probability.

Terms such as "engageable with," "engaged with," and "engaging" are intended to describe a structural connection between two or more elements. Some structural connections may be "fixedly engageable" and thus non-rotatable, as when the two or more elements are formed together and cannot be rotated independently without damage. Other structural connections may be "rotatably engageable," as when the two or more elements are coupled together by attachment elements (e.g., pins, screws, etc.) and/or linking elements (e.g., joints, hinges, etc.) allowing for independent rotation. Unless stated otherwise, the term engageable and its equivalents may comprise any such variations.

Aspects of any exemplary controller are described. The controller may comprise any type of software and/or hardware. Functional terms such as "processing," "computing," "calculating," "determining," "displaying," and the like, may refer to actions and processes performable the controller.

The software may comprise program objects (e.g., blocks of codes) executable by the controller to perform various functions. Each program object may comprise a sequence of operations leading to a desired result, such as an algorithm. The operations may require or involve physical manipulations of physical quantities, such as electrical or magnetic signals capable of being stored, transferred, combined, compared, and otherwise manipulated. The signals may be described conceptually as bits, characters, elements, numbers, symbols, terms, values, or the like.

The hardware may comprise any known computing and/or networking devices that are specially or generally configured to execute the program objects, perform the operations, and/or send or receive the signals. The hardware may comprise a processor that executes the project objects by manipulating and/or transforming input data represented as physical (electronic) quantities within the unit's registers and memories into output data similarly represented as physical quantities within the unit's memories or registers and/or other data storage, transmission, or display devices. The processor may comprise any number of processing element(s), including any singular or plural computing resources disposed local to or remote from one another. The program objects may be stored in any machine (e.g. computer) readable storage medium in communication with the processing unit, including any mechanism for storing or transmitting data and information in a form readable by a machine (e.g., a computer). Exemplary storage mediums may comprise: read only memory ("ROM"); random access memory ("RAM"); erasable programmable ROMs ("EPROMs"); electrically erasable programmable ROMs ("EEPROMs"); magnetic or optical cards or disks; flash memory devices; and/or any electrical, optical, acoustical or other form of propagated signals (e.g., carrier waves, infrared signals, digital signals, etc.).

Some functions are described with reference to method steps performable with the controller. The steps may define an exemplary sequence of operation, the order of which may be important. For example, a particular order of any method steps may describe a particular sequence of operation that is performable by the controller to realize specific processing benefits, such as improving a computational performance and/or an operational efficiency of the controller.

System 10

Aspects of this disclosure are now described with reference to an exemplary system 10 for maintaining healthy plankton populations in a culture medium 1, such as fresh water, saltwater, and anything added thereto. As shown in FIG. 1, for example, system 10 may comprise: a culture tank 20; a removal apparatus 30; a filtration apparatus 80; a treatment system 140; and a controller 180.

Culture Tank 20

Figure 2:
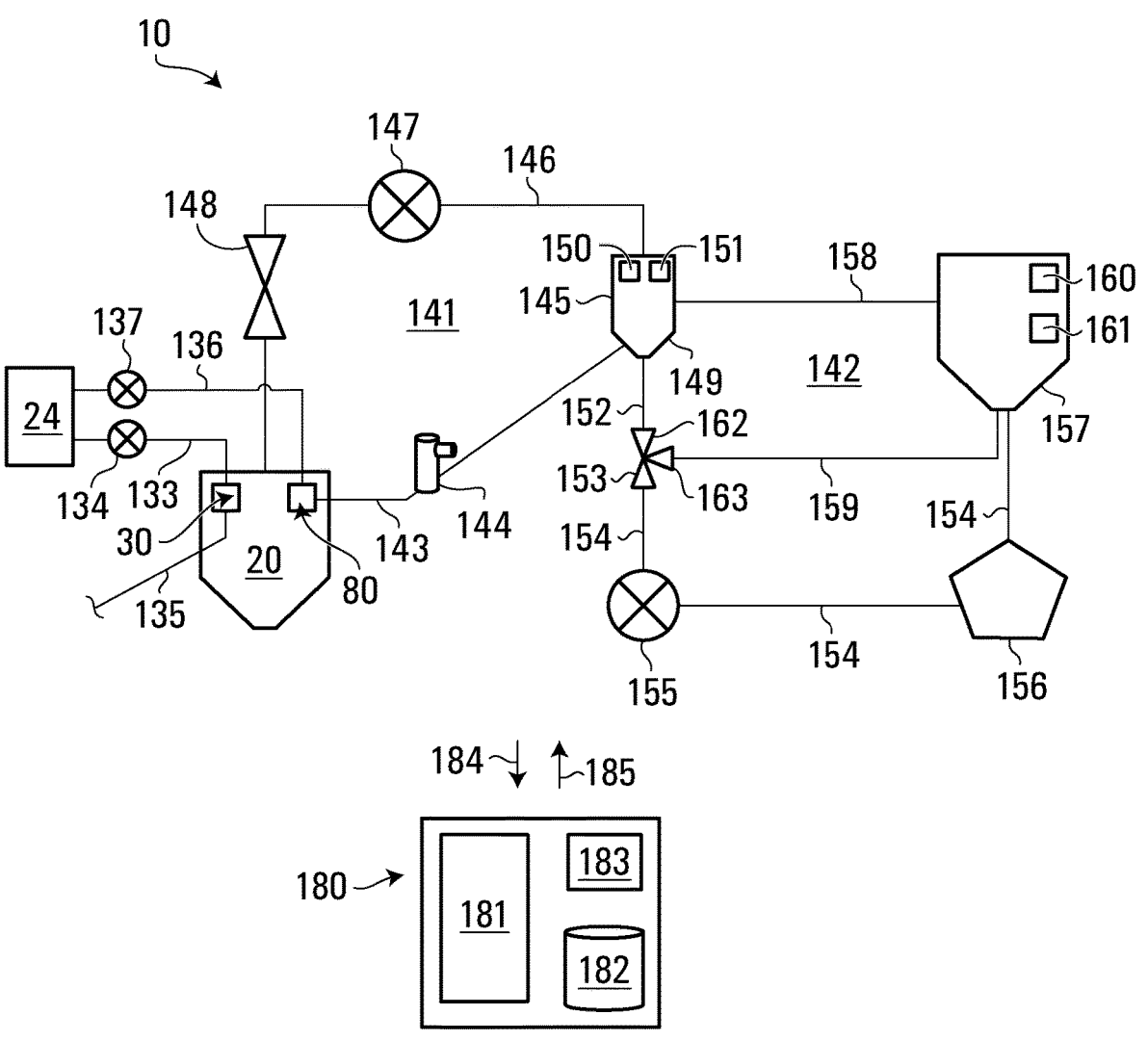
FIG. 2 depicts a flow diagram for the FIG. 1 system.

Culture tank 20 may comprise a free-standing vessel composed of any metallic and/or polymeric material suitable for containing a volume of a culture medium 1. As shown in FIGS. 1 and 2, for example, culture tank 20 may comprise a body 21, a flange 22, a frame 23, and a fluid source 24. Body 21 may comprise any shape sized to contain a volume of culture medium 1 (e.g., such approximately 1,000 L).

Flange 22 may extend outwardly from body 21 and comprise supports, such as supports 25 for removal apparatus 30 and supports 26 for filtration apparatus 80. Supports 25 and 26 may comprise notches extending through portions of flange 22 and body 21. Frame 23 may comprise structural elements adapted to support culture tank 20 and a ground surface. As shown in FIG. 2, for example, fluid source 24 may comprise piping, pumps, and/or vessels adapted to input one or more fluids to culture tank 20, apparatus 30, and/or apparatus 80.

Removal Apparatus 30

Figure 3:
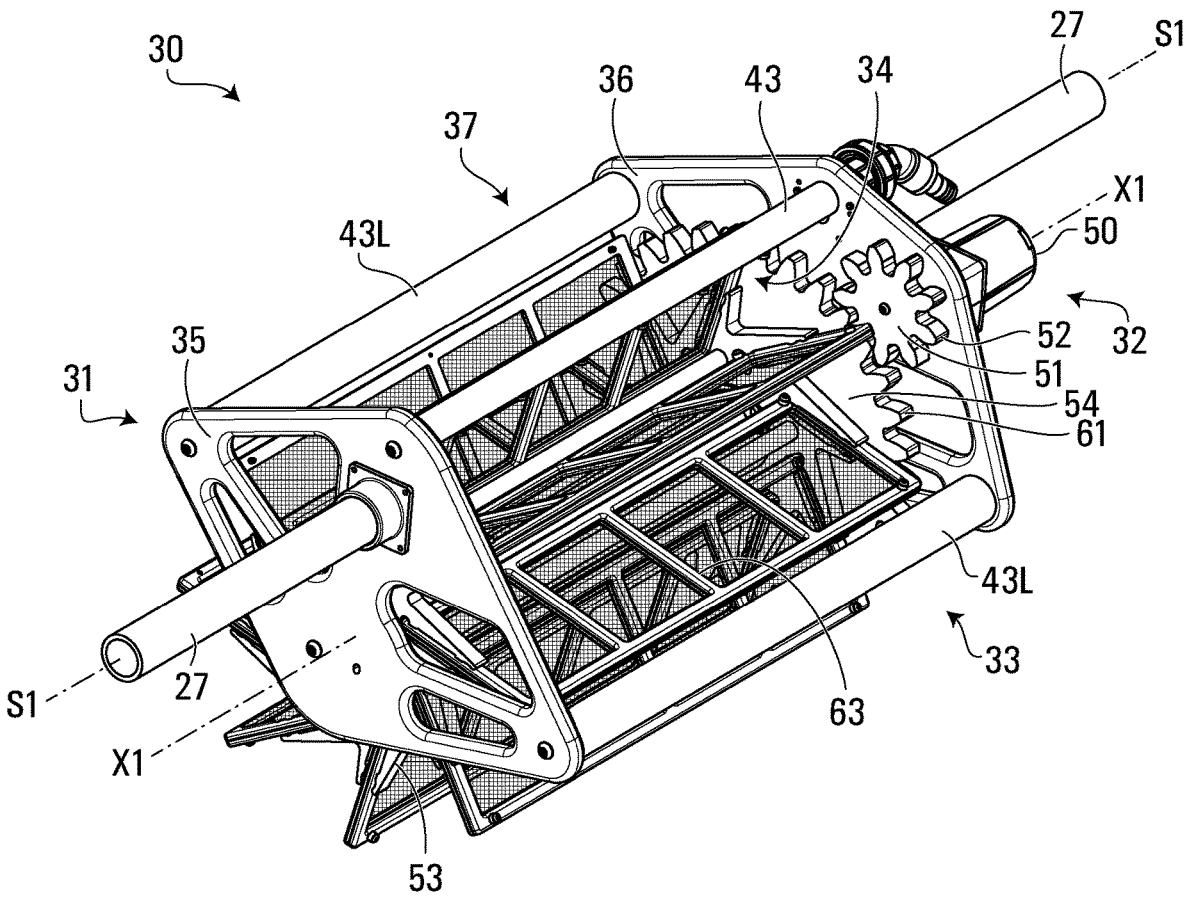
FIG. 3 depicts an exemplary apparatus for maintaining healthy plankton populations.

Removal apparatus 30 may output an effluent flow comprising particles that have been lifted out of culture medium 1 (the "effluent flow"). The particles may comprise uneaten rotifer food, decomposing matter, and the like. As shown in FIG. 3, for example, removal apparatus 30 may comprise a frame 31, a drive element 32, a filter body 33, and one or more nozzles 34.

As shown in FIGS. 3-8 and 23, for example, removal apparatus 30 may be operated to maintain a plankton population in culture medium 1 by removing particles from culture medium 1 according to a method (400) comprising: (i) rotating a filter body 33 to (a) lift the particles from culture medium 1 with a filter of filter body 33, and (b) position the filter relative to a conduit so that a first portion of the lifted particles fall into the conduit (410); (ii) directing a removal fluid toward filter body 33 to move a second portion of the lifted particles off the filter and into the conduit with impact forces applied by the removal fluid (420); and (iii) outputting an effluent flow from the conduit, the effluent flow comprising the first and second portions of the lifted particles and a portion of the removal fluid (430). Various aspects of removal apparatus 30 may be thus adapted to maintain the plankton population in culture medium 1 by removing particles from culture medium 1 according to this method.

Figure 4:
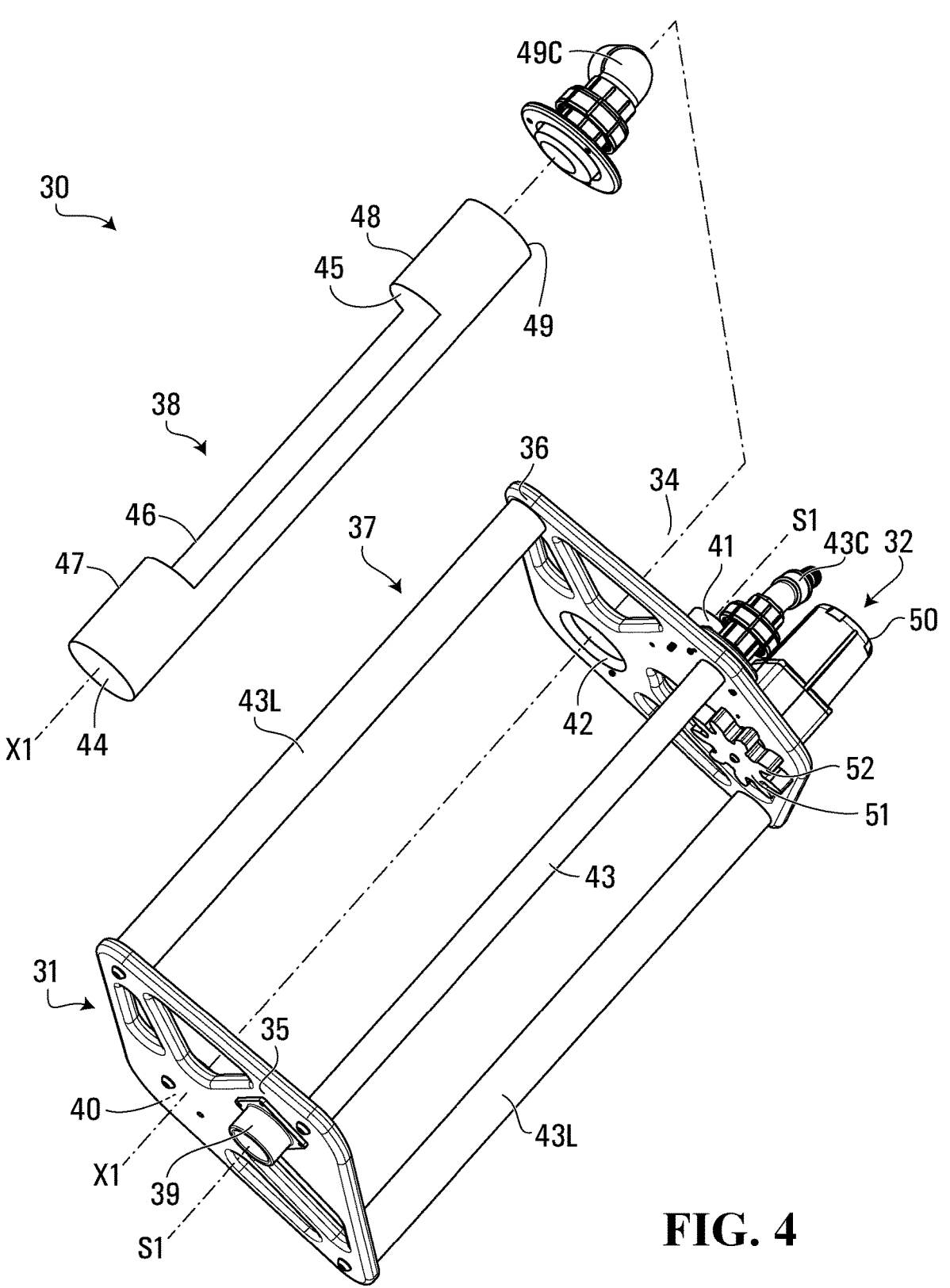
FIG. 4 depicts a frame for the FIG. 3 apparatus.
Figure 5:
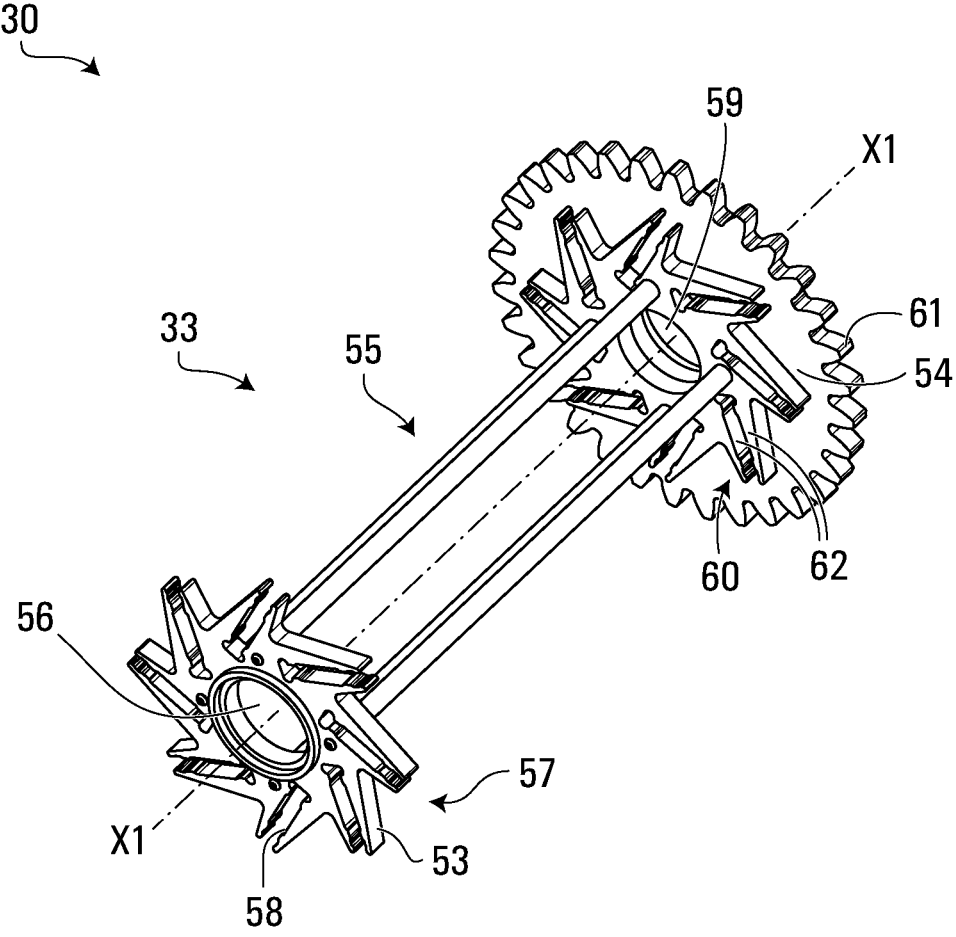
FIG. 5 depicts a filter body and an outlet post for the FIG. 3 apparatus.

Frame 31 may engage removal apparatus 30 with culture tank 20 (e.g., FIGS. 1 and 2) and provide rotational surfaces for filter body 33. As shown in FIGS. 4 and 5, for example, frame 31 may comprise a plate 35, a plate 36, posts 37, and an outlet post 38. Plate 35 may comprise a frame mount 39 and a filter socket 40. Frame mount 39 may be engaged with an exterior surface of plate 35 and comprise a post 27 (e.g., FIGS. 1 and 3) extending outwardly from plate 35. Filter socket 40 may comprise an opening extending at least partially into an interior surface of plate 35 to receive a first end of outlet post 38. Plate 36 may comprise a frame mount 41 and a filter socket 42. Frame mount 41 may be engaged with an exterior surface of plate 36 and comprise a post 27 (e.g., FIGS. 1 and 3) extending outwardly from plate 36. Filter socket 42 may comprise an opening extending through plate 36 to receive as second end of post 38.

Posts 37 may extend between frame plates 35 and 36. As used herein, the term "post" (e.g., as in posts 37) may comprise any structural elements, hollow or solid, include any type of beam or beam-like elements. As shown in FIG. 4, for example, posts 37 may include an upper post 43 and lower posts 43L engaged with plates 35 and 36 to form a rigid structure with an interior cavity. When this rigid structure is formed, frame mount 39 may be aligned with frame mount 41 along a support axis S1-S1 and filter socket 40 may be aligned with filter socket 42 along a filter axis X1-X1.

Figure 8:
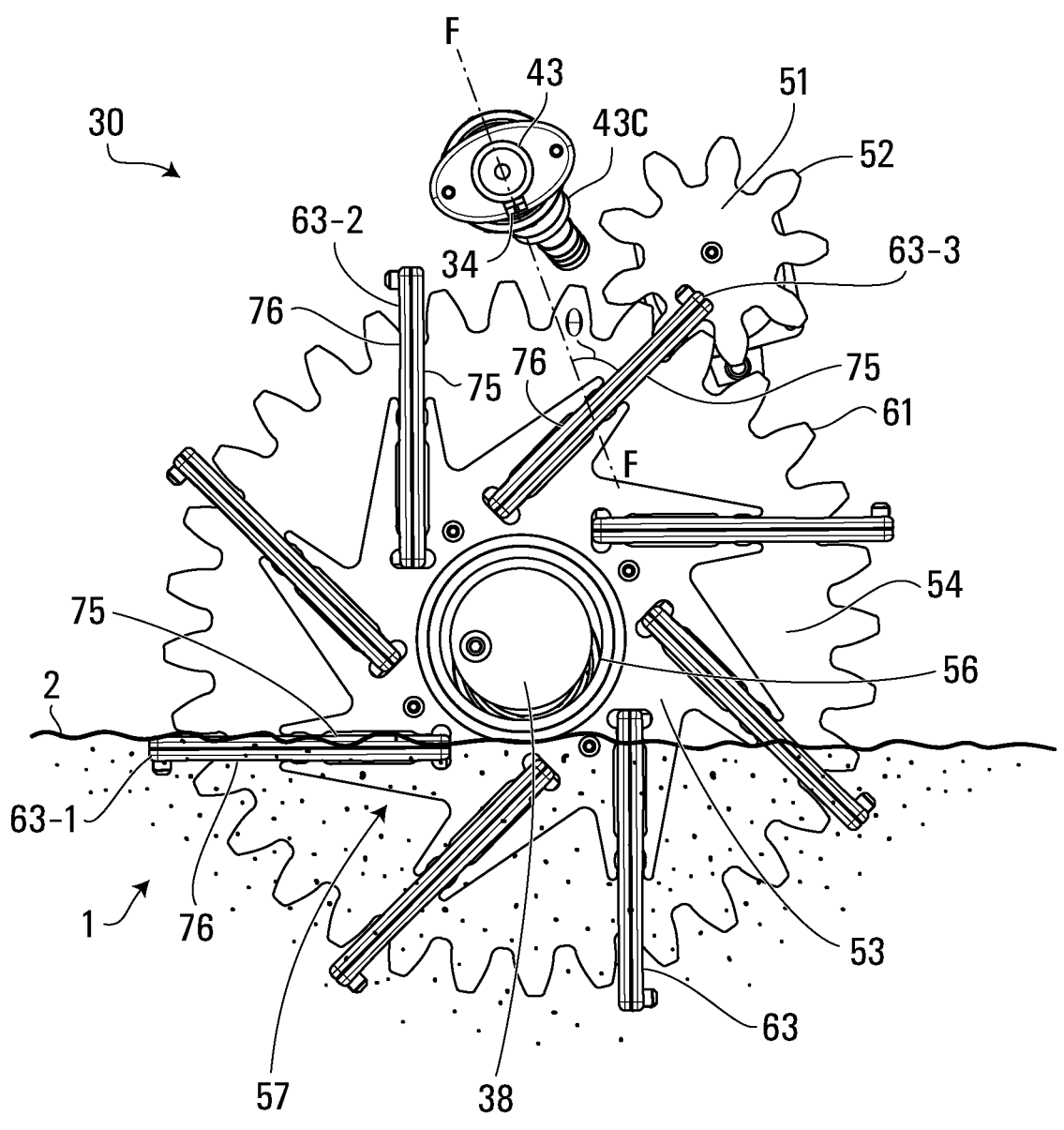
FIG. 8 depicts an operational view of the FIG. 3 apparatus.

One or more nozzles 34 may be located on upper post 43. As shown in FIG. 3, for example, upper post 43 may comprise a tube wall extending between frame plates 35 and 36, and a conduit extending through the tube wall. Each nozzle 34 may comprise a base engaged with the tube wall, an inlet positioned in the conduit, and an outlet directed toward the interior cavity of frame 31. As shown in FIG. 8, for example, each outlet of each nozzle 34 may direct the removal fluid toward the interior cavity of frame 31 along a different flow path F-F. The removal fluid may comprise any combination of water, air, and/or other agent deliverable with fluid source 24 (e.g., FIG. 2). As shown in FIG. 4, for example, a closed end of upper post 43 may be adjacent plate 35; and an open end of post 43 may be adjacent plate 36 and comprise a coupler 43C adapted to input the removal fluid from fluid source 24.

Outlet post 38 may output the effluent flow to a disposal system. As shown in FIG. 4, for example, outlet post 38 may comprise closed end 44, a conduit 45, an input opening 46, a bearing surface 47, a bearing surface 48, and open end 49. Conduit 45 may extend between closed end 44 and open end 49. Input opening 46 may extend into conduit 45 through an upper portion of outlet post 38 located between its bearing surfaces 47 and 48. As shown in FIG. 5, for example, input opening 46 may comprise an elongated opening with a cross-sectional area that extends along filter axis X1-X1 and is oriented towards one or more nozzles 34 to capture as much of the effluent flow as possible. As shown in FIG. 4, for example, open end 49 may comprise a coupler 49C adapted to establish a fluid communication with a disposal system, such as a floor drain.

Drive element 32 may comprise an electric motor 50 and a gear 51. As shown in FIG. 4, for example, electric motor 50 may be engaged with plate 36 and comprise a drive shaft extending through an opening of plate 36 when mounted thereto. Electric motor 50 may rotate the drive shaft relative to plate 36 responsive to control signals 185 from controller 180 (e.g., FIG. 2). Gear 51 may comprise an interior portion engaged with the drive shaft of motor 50 and exterior portion comprising teeth 52.

As shown in FIG. 5, for example, filter body 33 may comprise a plate 53, a plate 54, and posts 55. Plate 53 may comprise a bearing opening 56 and structures defining arms 57 extending outwardly therefrom. Each arm 57 may comprise a mounting slot 58 comprising an open or closed shape. Plate 54 may comprise a bearing opening 59, structures defining arms 60 extending outwardly therefrom, and an outer portion comprising teeth 61. Each arm 60 may comprise a mounting slot 62 comprising an open or closed shape. As shown in FIG. 5, for example, mounting slots 58 and 62 may comprise jaws defining open channels therebetween and opposing interior surfaces that are biased toward one another by the structures defining arms 57 and 60. Posts 55 may extend between plates 53 and 54 to form a rigid structure with an interior cavity. As shown in FIG. 5, for example, when the rigid structure of filter body 33 is formed, bearing openings 56 and 59 may be aligned with filter axis X1-X1, and mounting slots 58 and 62 may be aligned with an axis that is parallel to axis X1-X1.

Figure 7:
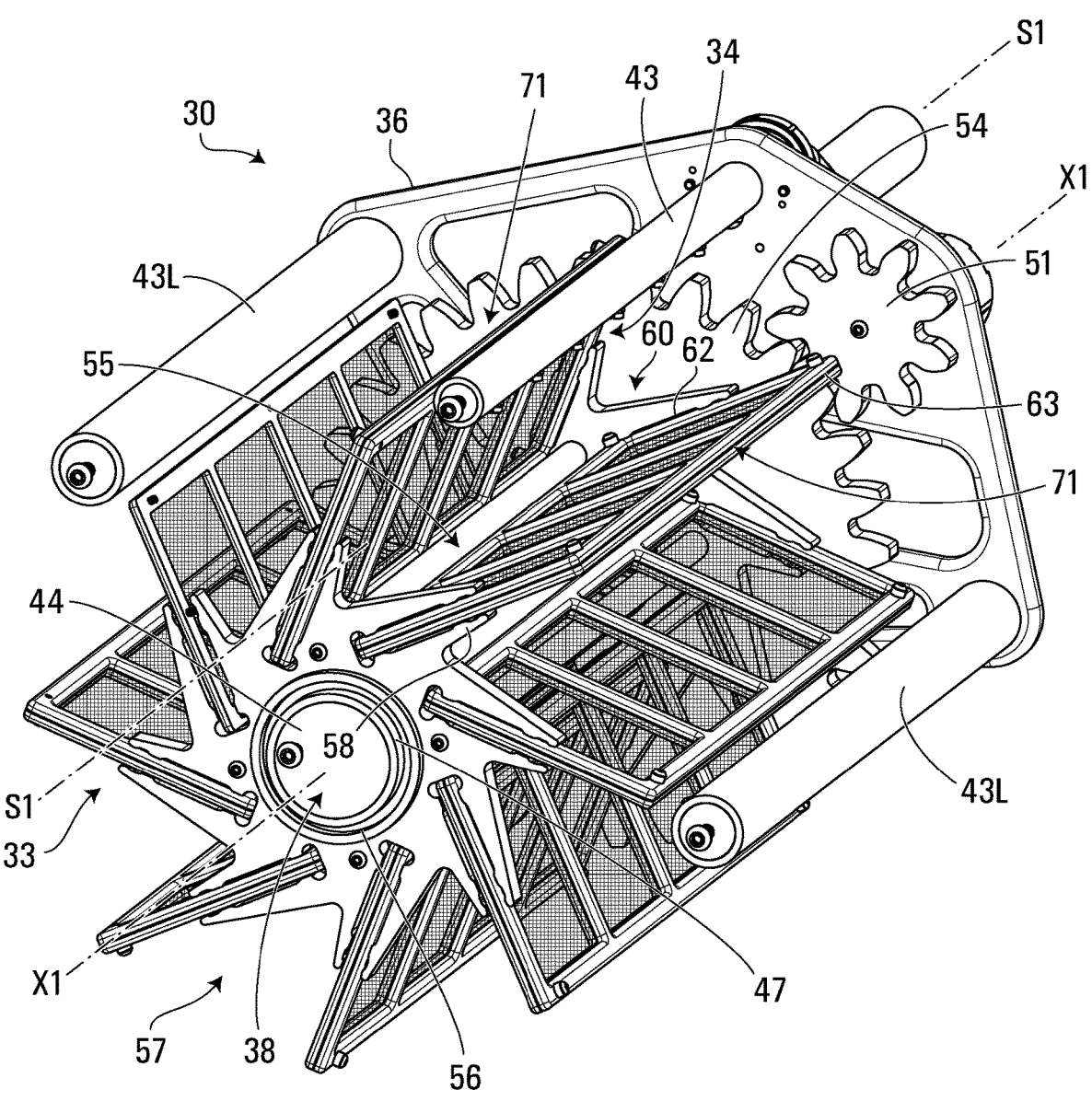
FIG. 7 depicts a partially assembled view of the FIG. 3 apparatus.

The filter may comprise one or more filter panels 63 that are engaged with filter body 33 and moved therewith to lift the particles out of culture medium 1. As shown in FIG. 5, for example, filter body 33 may comprise eight sets of arms 57 and 60, having eight sets of mounting slots 58 and 62, allowing for eight different filter panels 63 to be engaged with filter body 33. Any number of filter panels 63 may be used. As shown in FIGS. 5 and 7, for example, opposite ends of each filter panel 63 may be engaged with one set of mounting slots 58 and 62 so that each filter panel 63 may be rotated with simultaneously filter body 33 about filter axis X1-X1.

Figure 6:
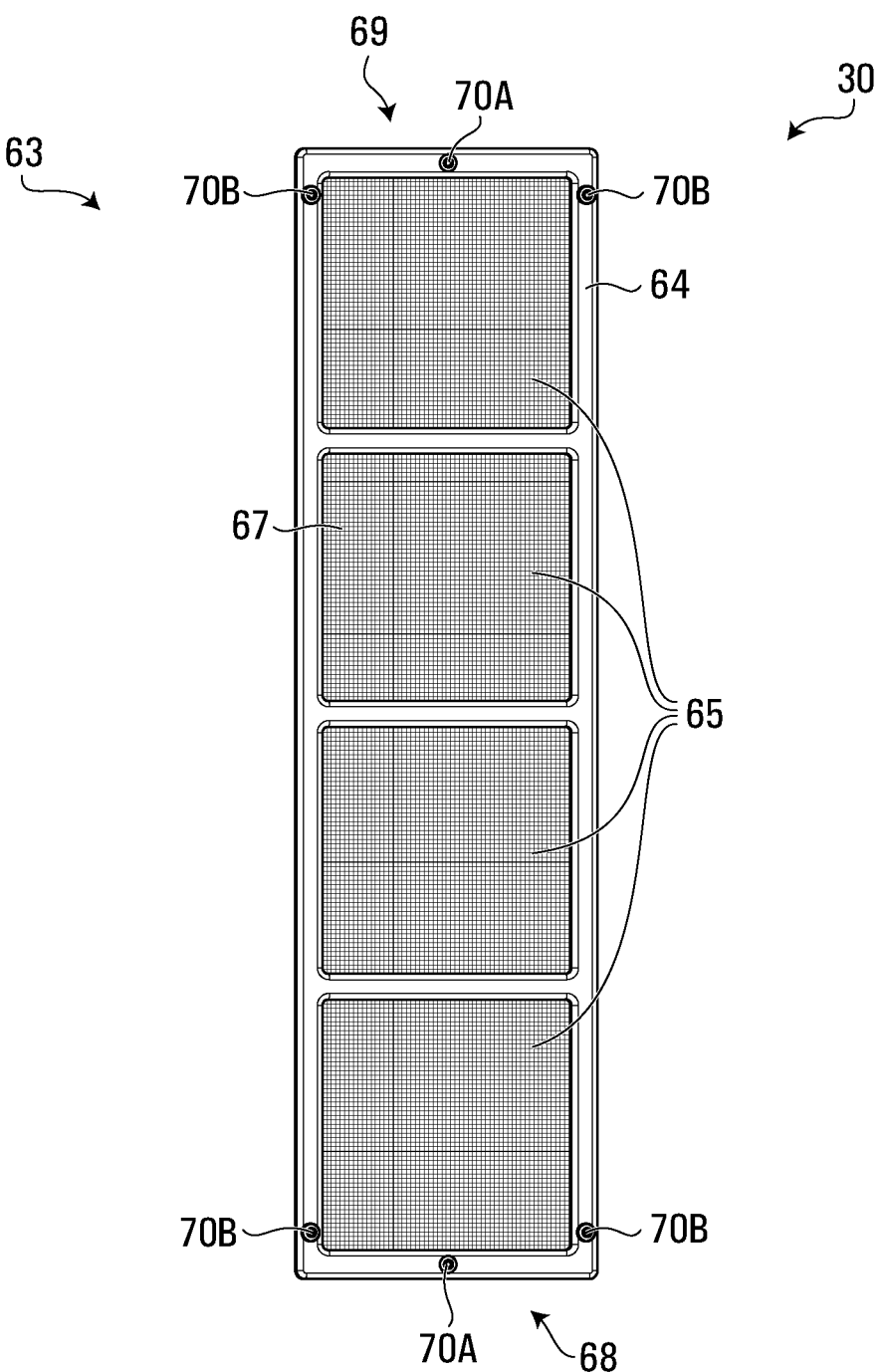
FIG. 6 depicts a filter for the FIG. 3 apparatus.

As shown in FIG. 6, for example, each filter panel 63 may comprise a filter panel frame 64 and a porous element 65. Each filter panel frame 64 may be optimized for weight and rigidity to increase the efficiency of removal apparatus 30, and for optimal positioning of porous element 65 relative to culture medium 1 and/or one or more nozzles 34. Each filter panel frame 64 may comprise beam elements spanning between plates 53 and 54. The beam elements may resist deflections caused by drag forces associated with culture medium 1, gravity forces associated with a weight of filter panel 63 any suspended particles being lifted therewith, and impact forces associated with the removal fluid. As shown in FIG. 6, for example, filter panel frame 64 may define section openings and porous element 65 may comprise one or more elements spanning across the section openings. Porous element 65 may be inserted between portions of each filter panel 63 and maintained at a fixed position relative thereto. As shown in FIG. 6, for example, porous element 65 may be located between first and second sub-frames of filter panel frame 64 and maintained in the fixed position by engaging edge portions of the sub-frames with one another and porous element 65 using attachment elements (e.g., screws). Alternatively, porous element 65 also may be secured to filter panel frame 64 without additional attachment elements, such as with adhesives and/or by using molding techniques, such as over molding.

As shown in FIG. 6, for example, porous element 65 may comprise a grid with openings 67 sized to lift suspended particles of a certain size from culture medium 1 while allowing flows of culture medium 1 to pass through. A mesh material, a fibrous pad, or a similar structure may be used to define the grid. For example, the grid may made from rotifer floss, which is a loose weave filter material (e.g., made from nylon or other polymeric material) that allows culture medium 1 to easily pass through, but has a high surface area to which detritus sticks to. Each opening 67 may comprise a maximum width larger than some of the plankton (e.g., most rotifers), such as a maximum width of approximately 0.5 mm or greater, or between approximately 0.5 mm and approximately 1.0 mm, or less than approximately 2.0 mm. Porous element 65 also may comprise one or more layers of any such materials. For example, each porous element 65 may comprise a first layer of nylon mesh having openings 67 with a maximum width of approximately 0.5 mm, a second layer of nylon mesh having openings 67 with a maximum width of approximately 1.5 mm, and a third layer of nylon mesh having openings 67 with a maximum with of approximately 0.5 mm. When its openings 67 are sized accordingly, each porous element 65 may thus be adapted to lift any suspended particles having a width greater that the maximum width of is openings 67, such as uneaten portions of plankton food, while minimizing the amount of plankton lifted therewith. Smaller openings 67 may be used to remove some of the plankton.

Each filter panel 63 may comprise self-locating and/or locking features that allow for easy replacement. One end of filter panel 63 may comprise locating features 68 and the other end of filter panel 63 may comprise locating features 69. Locating features 68 and 69 may comprise surfaces that are engageable with surfaces of filter body 33 to maintain a position of filter panel 63. As shown in FIG. 6, for example, locating features 68 and 69 may comprise protrusions extending outwardly from one or both sides of each filter panel 63, including a rounded protrusion 70A adjacent a short side of each filter panel 63 and protrusions 70B offset from the short side of each panel 63.

Removal apparatus 30 may be assembled to prevent binding of filter body 33 and/or limit deflections of filter panels 63 when moving through culture medium 1, and to maintain an alignment between one or more nozzles 34 and input opening 46. As shown in FIGS. 3 and 7, for example, removal apparatus 30 may be assembled by a method comprising: assembling frame 31; assembling filter body 33; engaging filter body 33 with outlet post 38; engaging post 38 with frame 31; engaging drive element 32 with frame 31 and filter body 33; and engaging filter panels 63 with filter body 33.

Frame 31 may be assembled by engaging opposite ends of posts 37 with interior surfaces of frame plates 35 and 36. As shown in FIG. 4, for example, the opposite ends of upper post 43 and lower posts 43L may be engaged with the interior surfaces of plate 35 and 36 by inserting a threaded attachment element (e.g., a screw) into a threaded opening of each opposite end through an opening in plate 35 or 36. Frame mounts 39 and 41 may be similarly engaged with exterior surfaces of frame plates 35 and 36.

As shown in FIG. 5, for example, filter body 33 may be assembled by engaging opposite ends of each post 55 to plates 53 and 54 in a manner similar to posts 37.

Outlet post 38 may be engaged with filter body 33 by locating filter body 33 in the interior cavity of frame 31 so that bearing openings 56 and 59 are aligned with filter axis X1-X1, inserting closed end 44 into filter socket 42, moving closed end 44 towards plate 35 along axis X1-X1 until it passes through bearing openings 56 and 59 and enters filter socket 40, and inserting a threated attachment element (e.g., a screw) into a threaded opening of closed end 44 through an opening in plate 35 to fix a position of outlet post 38 relative to frame 31. Bearing surface 47 may now be adjacent bearing opening 56 and bearing surface 48 may now be adjacent bearing opening 59. Filter body 33 may then be rotated in the interior cavity of frame 31 on outlet post 38 about filter axis X1-X1 by allowing interior surfaces of bearing openings 56 and 59 to rotate relative to frame 31 on bearing surfaces 47 and 48. As shown in FIG. 5, for example, outlet post 38 may extend along filter axis X1-X1 so that any suspended particles directed into input opening 46 may flow into conduit 45 and out of open end 49 along filter axis X1-X1 while filter body 33 is rotating about axis X1-X1. Coupler 49C may then direct the suspect particles into the waste disposal system.

As shown in FIG. 4, for example, drive element 32 may be engaged with frame 31 and filter body 33 by engaging electric motor 50 to an exterior surface of plate 36 so that the drive shaft of motor 50 extends through an opening extending through plate 36. As shown in FIG. 3, for example, an interior diameter of gear 51 may then be engaged with the drive shaft of motor 50 so that teeth 52 of gear 51 may be meshed with teeth 61 of plate 54, allowing gear 51 and thus filter body 33 to be rotated about filter axis X1-X1 independently of frame 31 with electric motor 50 responsive to control signals 185 from controller 180 (e.g., FIG. 2).

As shown in FIG. 7, for example, each filter panel 63 may be engaged with filter body 33 by aligning a long side of each panel 63 with mounting slots 58 and 62 of arms 57 and 60, and pushing the long side into slots 58 and 62 in a direction 71 that is generally parallel with each slot 58 and 62. The pushing may spread the opposing interior surfaces of the jaws of slots 58 and 62 apart from another, allowing each panel 63 to be advanced into mounting slots 58 and 62 in direction 71 until its locating features 68 and 69 are engaged with surfaces of arms 57 and 60. As shown in FIGS. 6 and 7, for example, each filter panel 63 may be pushed in direction 71 until its protrusions 70A are snapped into an indented portion of each mounting slot 58 or 62, and its protrusions 70B are positioned against interior surfaces of each arm 57 or 60. In this configuration, protrusions 70A may interact with the indented portions of slots 58 and 62 to prevent filter panel 63 from being pulled out of slots 58 and 62 in direction 71; and protrusions 70B may interact with the interior surfaces of arms 57 and 60 to maintain a lateral position of filter panel 63 along filter axis X1-X1. Each filter panel 63 may thus be engaged with filter body 33 in a single step, i.e., by pushing its long side into mounting slots 58 and 62 in direction 71 until its locate features 68 and 69 are snapped into position, and disengaged from body 33 in an opposite manner, greatly simplifying the installation and removal of panels 63 for maintenance purposes. The indented portions of slots 58 and 62 may define similar attachment features, and the location and shape of protrusions 70A and 70B may likewise define a correspondingly similar features, allowing each filter panel 63 to be installed in slots 58 and 62 in at least four different orientations to prevent user error and further simplify installation.

Once removal apparatus 30 has been assembled, it may be rendered operational by a method comprising: mounting removal apparatus 30 to culture tank 20; establishing fluid communications between culture tank 20, one or more nozzles 34, outlet post 38, and treatment system 140; and establishing data communications between communicable elements of removal apparatus 30 and controller 180.

Removal apparatus 30 may be engaged with culture tank 20 to prevent culture medium 1 from flowing into the waste disposal system, and to limit biofouling by minimizing a surface area of filter body 33 and/or each filter panel 63 in culture medium 1 at any time. As shown in FIG. 1, for example, frame 31 may be engaged with culture tank 20 by placing posts 27 in the notches of supports 25 so that the weight of removal apparatus 30 may be supported on body 21 with posts 27. As shown in FIGS. 1 and 8, for example, frame 31 may be adapted to keep outlet post 38 out of culture medium 1 so that only a lower portion of filter body 33 and filter panels 63 may be submerged in the culture medium at any one time to limit biofouling of filter body 33, filter panels 63, and any components related thereto. As shown in FIG. 8, for example, top surface 2 of culture medium 1 may be maintained at a level relative to a lower portion of filter body 33 under outlet post 38 so that only one filter panel 63 may be completely submerged in culture medium 1 at a time. Additional panels 63 may be submerged by changing the geometric alignment of filter axis X1-X1 relative to top surface 2 of culture medium 1.

A first fluid communication may be established between one or more nozzles 34 and a fluid source 24. As shown in FIG. 2, for example, fluid source 24 may comprise a line 133 and a pump 134. Line 133 may be coupled to a pump and/or vessel operable to output the removal fluid to one or more nozzles 34 at a desired pressure (e.g., approximately 10-20 psi). The first fluid communication may be established by engaging coupler 43C (e.g., FIG. 4) with line 133 (e.g., FIG. 2). Pump 134 may be located on coupler 43C and/or on a portion of line 133 in advance of one or more nozzles 34; and operable to control a flow rate of the removal fluid responsive to control signals 185 from controller 180 (e.g., FIG. 2).

A second fluid communication may be established between outlet post 38 and the disposal system, such as the aforementioned floor drain. As shown in FIG. 2, for example, the second fluid communication may be established by engaging open end 49 with a line 135 that directs the effluent flowing through conduit 45 to the disposal system.

The communicable elements of removal apparatus 30 may comprise drive element 32, pump 134, and one or more sensors position on or about apparatus 30. Data communications may be established between each controllable element and controller 180 using any known communication technologies. As shown in FIG. 2, for example, the data communications may be established by connecting drive element 32 (e.g., FIGS. 3 and 4), pump 134, and the one or more sensors to controller 180 over a wired and/or wireless network so that any control data 184 and control signals 185 may be sent and received using a communication protocol.

Once removal apparatus 30 has been assembled and rendered operational, it may be continuously or intermittently rotated so that filter body 33 and filter panels 63 attached thereto are rotated a rate of between 2 and 3 RPM, or approximately 2.8 RPM. For example, removal apparatus 30 may be operated intermittently so that porous element 65 of one or more of panels 63 may lift clumps of floating particles (e.g., floating uneaten plankton food and dead plankton) out of culture medium 1, and nozzles 34 may be utilized to remove any portions of the floating particles that become stuck in openings 67 of that porous element 65 while lifting. As described above, removal apparatus 80 may be operated to cause movements of filter panel 63 between: (i) a lift position, in which a lift surface 75 of one filter panel 63 is generally parallel with top surface 2 of culture medium 1; (ii) a dump position, in which lift surface 75 of the one panel 63 is generally vertical and positioned vertically relative to conduit 45 and input opening 46; and (iii) a removal position, in which lift surface 75 of the one panel 63 faces conduit 45 and input opening 46 and a back surface 76 of the one panel 63 is positioned under one or more nozzles 34. As shown in FIG. 3, for example, drive element 32 may cause electric motor 50 to rotate gear 51 responsive to control signals 185 from controller 180, thereby causing gear 54 to rotate filter body 33 about filter axis X1-X1 so that each filter panel 63 is moved between the lift, dump, and removal positions responsive to controller 180.

The lift position may be utilized to maximize the ability of porous element 65 to lift particles out of culture medium 1. As shown in FIG. 8 with respect to an exemplary filter panel 63-1, for example, a lateral axis of each filter panel 63 may be offset from and not intersect filter axis X1-X1 so that a lift surface 75 of each panel 63 may be generally parallel to a top surface 2 of culture medium 1 when moved into the lift position, thereby maximizing the surface area of each porous element 65 that is available to lift suspended particles from culture medium 1. The dump position may be utilized to cause a first portion of the lifted particles to fall into conduit 45 through input opening 46 with gravity forces. As shown in FIG. 8 with respect to an exemplary filter panel 63-2, for example, the lift surface 75 of each filter panel 63 may be moved into a generally vertical position relative to conduit 45 and input opening 46 so that the first portion of the lifted particles slides and/or falls off its porous element 65 and into conduit 45 through input opening 46.

A second portion of the lifted particles may cling to porous element 65 and/or become lodged in its openings 67, making them difficult or impossible to remove with gravity forces. The removal position may be utilized to direct the second portion of the lifted particles into conduit 45 through input opening 46 with impact forces applied by the removal fluid output from one or more nozzles 34. As shown in FIG. 8 with respect to an exemplary filter panel 63-3, for example, each panel 63 may be rotated until its lift surface 75 is inverted over conduit 45 and input opening 46 so that its back surface 76 intersects a flow path F-F extending outwardly from each nozzle 34 at an intersecting angle θ. The removal fluid may be directed along flow path F-F in order to apply impact forces to back surface 76 at a pressure sufficient to push the second portion of the lifted particles away from lift surface 75 and into conduit 45 through opening 46. The removal fluid may pass across each back surface 76 at different intersecting angles θ when filter body 33 is rotated about filter axis X1-X1 in order to dislodge the particles from openings 67 with the impact forces applied by the removal fluid at each different intersecting angle θ.

The second fluid communication may continuously direct the effluent flow out of conduit 45 along filter axis X1-X1 and into a line 135 leading to the disposal system, which may be preferable to attempting to clean the effluent flow because of the high concentration of waste contained therein.

Filtration Apparatus 80

Filtration apparatus 80 may output a filtered flow of culture medium 1 (the "filtered flow") from any vessel containing high quantities of suspended particles that would clog a traditional filter.

Figure 9:
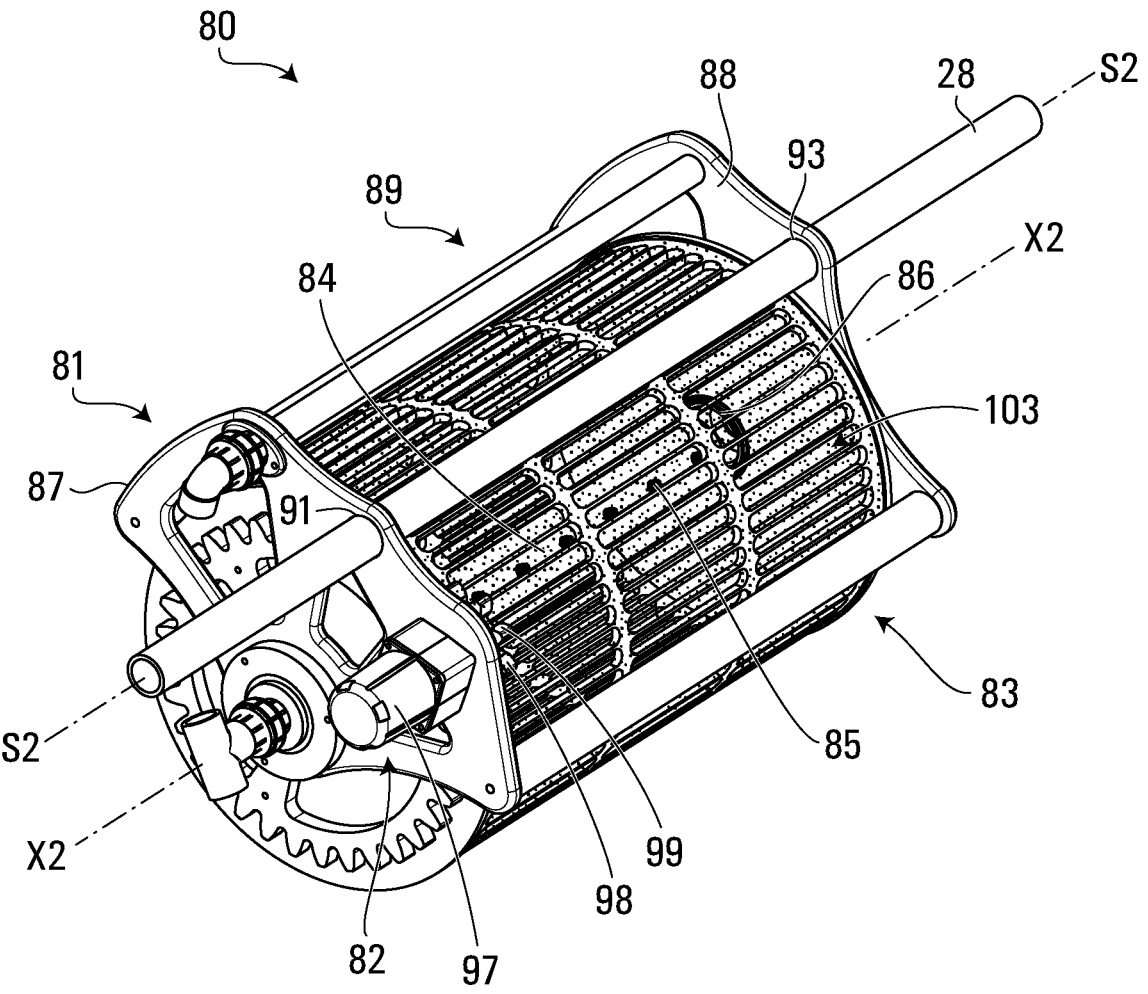
FIG. 9 depicts another exemplary apparatus for maintaining healthy plankton populations.

As shown in FIGS. 9-12 and 24, for example, filtration apparatus 80 may be operable to maintain a plankton population in culture medium 1 by filtering culture medium 1 according to a method 440 comprising: (i) moving a first area of a filter body into culture medium 1, the filter body defining an interior cavity and being adapted to keep plankton and particles out of the interior cavity while permitting culture medium 1 to pass into the interior cavity (450); (ii) passing a volume of culture medium 1 through the first area and into the interior cavity (460); (iii) outputting a filtered flow from a location in the interior cavity (470); (iv) rotating the filter body to: (a) remove the first area and any plankton and particles attached to the first area from the culture medium, and (b) move a second area of the filter body into culture medium 1 (480); and (v) directing a cleaning fluid toward the filter body to move the plankton and particles attached to the first area into the culture medium (490). The filtered flow may then be processed further with treatment system 140 (e.g., FIG. 2) and recirculated back into culture tank 20. Various elements may be adapted to maintain the plankton population in culture medium 1 by filtering culture medium 1 according to this method. As shown in FIG. 9, for example, filtration apparatus 80 may comprise a frame 81, a drive element 82, a filter body 83, an interior nozzle post 84, one or more nozzles 85, and an outlet post 86.

Figure 10:
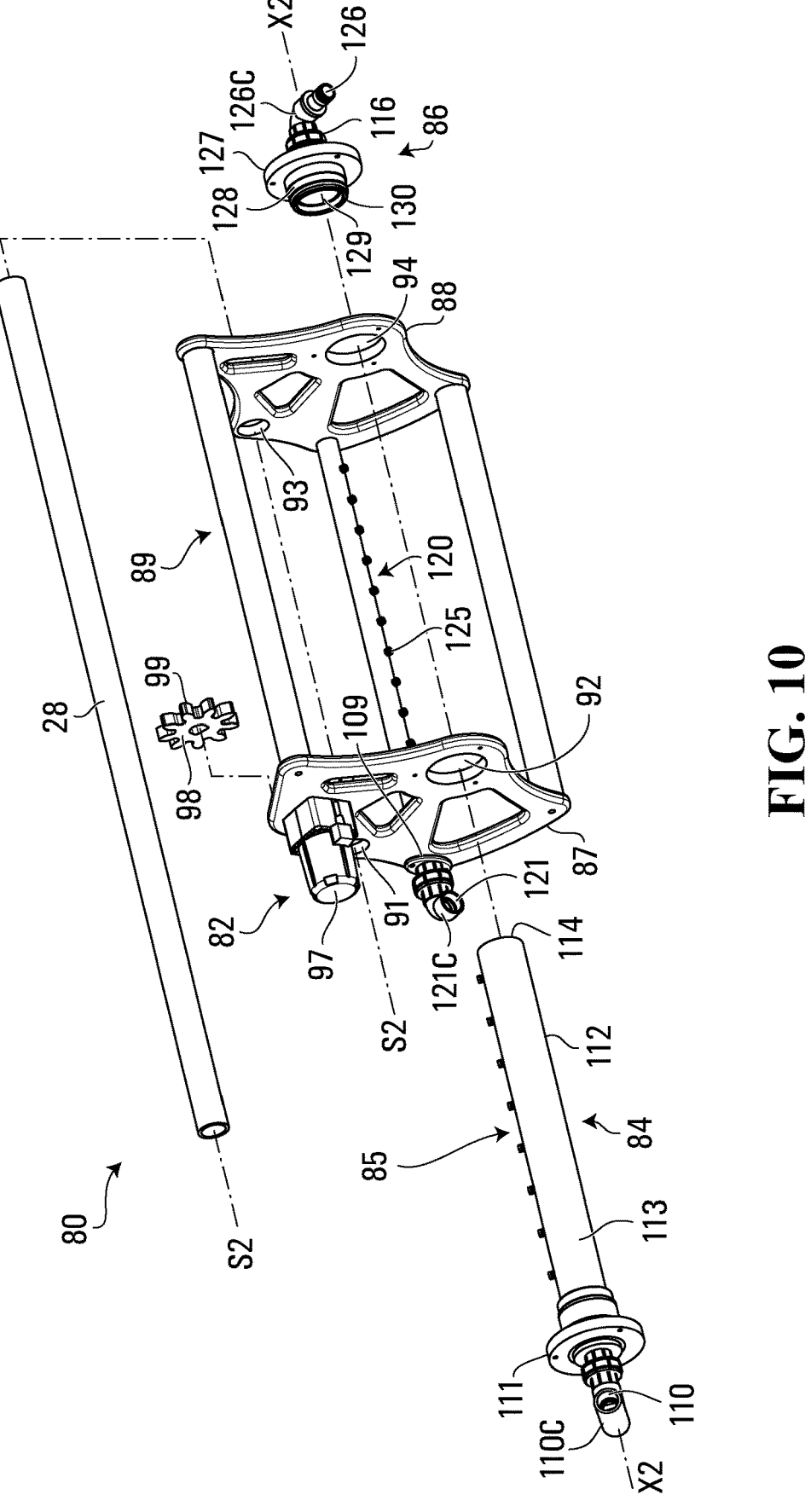
FIG. 10 depicts a frame, a nozzle post, an outlet post, and a support post for the FIG. 9 apparatus.

Frame 81 may engage filtration apparatus 80 with culture tank 20 and provide rotational surfaces for filter body 83. As shown in FIG. 10, for example, frame 81 may comprise a plate 87, a plate 88, and posts 89. Plate 87 may comprise a support opening 91, a bearing opening 92, and an exterior nozzle post opening 109. Plate 88 may comprise a support opening 93 and a bearing opening 94. Posts 89 may extend between frame plates 87 and 88 to form a rigid structure with an interior cavity. When the rigid structure is formed, support opening 91 may be aligned with support opening 93 along a support axis S2-S2 and bearing opening 92 may be aligned with bearing opening 94 along a filter axis X2-X2.

Drive element 82 may comprise an electric motor 97 and a gear 98. As shown in FIG. 10, for example, electric motor 97 may be engaged with plate 87 and comprise a drive shaft extending through an opening of plate 87 when mounted thereto. Electric motor 97 may rotate the drive shaft relative to plate 87 responsive to control signals 185 from controller 180 (e.g., FIG. 2). As shown in FIG. 10, for example, gear 98 may comprise an interior portion engaged with the drive shaft of motor 97 and outer portion comprising teeth 99 (e.g., FIG. 9).

Figure 11:
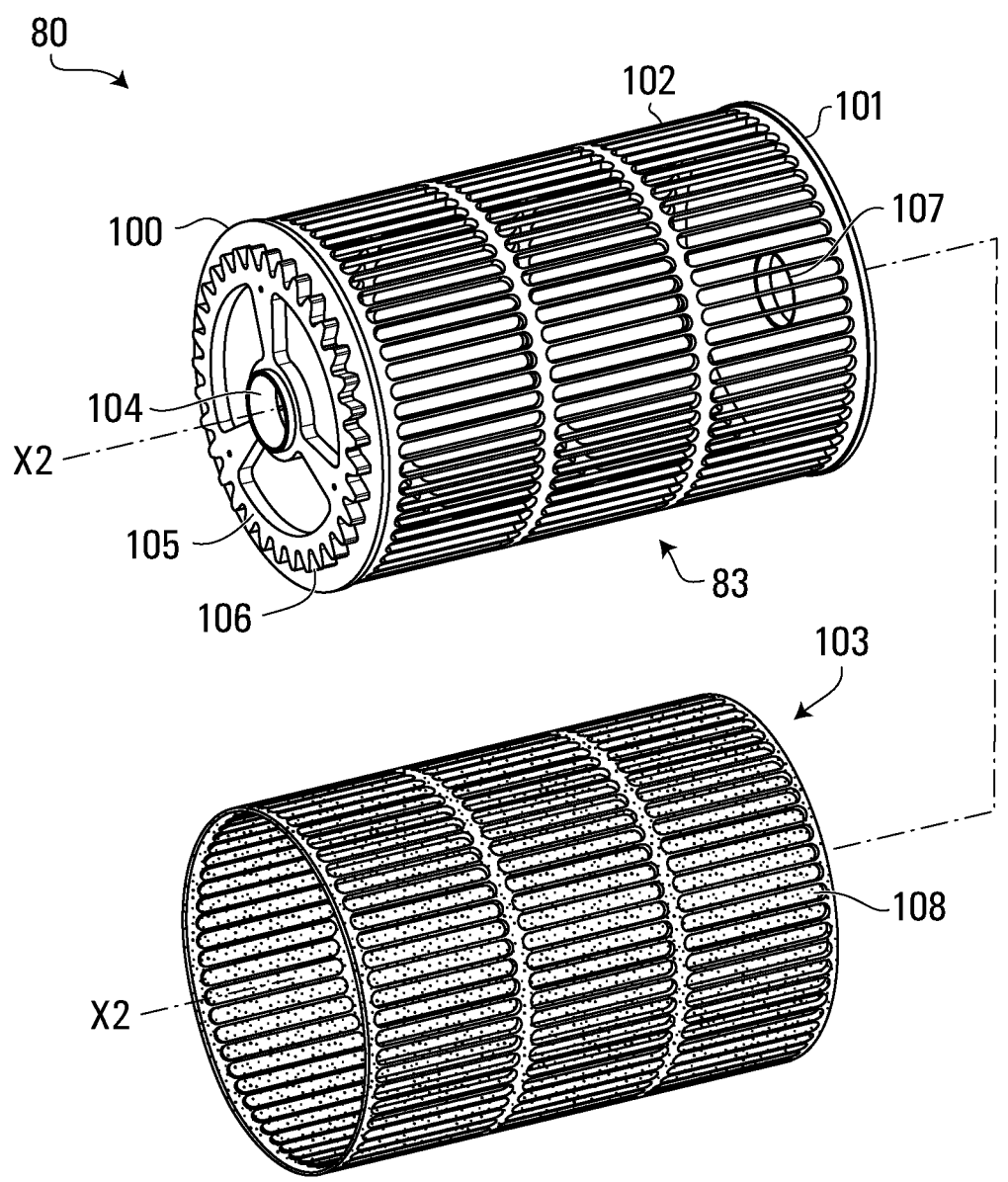
FIG. 11 depicts a filter body and a filter for the FIG. 9 apparatus.

As shown in FIG. 11, for example, filter body 83 may comprise a plate 100, a plate 101, a shell 102, and a porous element 103. Plate 100 may comprise a bearing sleeve 104 and a gear 105. Bearing sleeve 104 may be sized to receive interior nozzle post 84. Gear 105 may comprise an interior portion engaged with bearing sleeve 104, a back surface engaged with plate 100, and an exterior portion comprising teeth 106. Plate 101 may comprise a bearing opening 107 sized to receive outlet post 86. Shell 102 may extend between plates 100 and 101 to form a rigid structure with an interior cavity. When this rigid structure is formed, bearing sleeve 104 may be aligned with bearing opening 107 along filter axis X2-X2 when filter body 83 is located in the interior cavity of frame 81. As shown in FIG. 11, for example, shell 102 may define a cylindrical or barrel shape with elongated openings extending therethrough. This shape may resist deflections caused by drag forces applied to porous element 103 by culture medium 1; and gravity forces associated with a weight of filter body 83, porous element 103, and any particles attached thereto.

Porous element 103 may surround the interior cavity of filter body 83 by wrapping around shell 102 and/or spanning between its openings. Porous element 103 may comprise a sponge-like material defining openings 108 sized to keep suspended particles in culture medium 1 out of the interior cavity of filter body 83. The spongy material may comprise a web or matrix of fibers that are formed and/or woven together so that each opening 108 has an irregular shape. As shown in FIG. 11, for example, each opening 108 may comprise a maximum width smaller than most rotifers, such as a maximum width of approximately 0.044 mm, or approximately 0.5 mm or less, or between approximately 0.5 mm and approximately 0.01 mm. When its openings 108 are sized accordingly and unclogged, porous element 103 may keep any particles in culture medium 1 having a width greater that the maximum width out of the interior cavity of filter body 83 while simultaneously allowing flows of culture medium 1 to pass into the interior cavity. As also shown in FIG. 11, for example, porous element 103 may comprise elongated protrusions that are receivable in the elongated openings of shell 102. The elongated protrusions may be molded into or formed out of the spongy material.

Figure 12:
FIG. 12 depicts a cross-sectional view of the FIG. 9 apparatus.

Interior nozzle post 84 may extend into the interior cavity of filter body 83 and be positioned to direct the cleaning fluid toward interior surfaces of filter body 83. As shown in FIG. 12, for example, interior nozzle post 84 may comprise an open end 110, a flange 111, an extension 112, a conduit 113, and a closed end 114. Open end 110 may comprise a coupler 110C adapted to input the cleaning fluid from fluid source 24. An exterior surface of extension 112 may be receivable in bearing opening 92 and bearing sleeve 104 along filter axis X2-X2. Flange 111 may be engaged with plate 87 to secure extension 112 in bearing opening 92. As shown in FIG. 12, for example, the exterior surface of extension 112 may comprise a groove 116 sized to receive a seal 117 (e.g., an O-ring) that prevents culture medium 1 from passing between the exterior surface of extension 112 and interior surfaces of bearing sleeve 104. Extension 112 may thus be securely cantilevered into the interior cavities of frame 81 and filter body 83 with flange 111. Conduit 113 may extend from open end 110 to closed end 114 through flange 111 and extension 112.

One or more nozzles 85 may be located on interior nozzle post 84. As shown in FIG. 10, for example, each nozzle 85 may comprise a base engaged with extension 112, an inlet positioned in conduit 113, and an outlet directed toward the interior surfaces of filter body 83. As shown in FIG. 12, for example, the cleaning fluid may be directed into conduit 113, through the inlet of each nozzle 85, and out of the outlet of each nozzle 85 toward the interior surfaces of filter body 83.

Filtration apparatus 80 also may comprise an exterior nozzle post 120. As shown in FIG. 12, for example, exterior nozzle post 120 may comprise an open end 121, an extension 122, a conduit 123, and a closed end 124. Open end 121 may comprise a coupler 121C adapted to engage extension 122 with plate 87 and input additional cleaning fluid from fluid source 24. Extension 122 may comprise a hollow one of posts 89. Conduit 123 may extend from open end 121 to closed end 124 through extension 122. Closed end 124 may engage extension 122 with plate 88.

One or more nozzles 125 may be located on exterior nozzle post 120. Each nozzle 125 may direct additional cleaning fluid toward exterior surfaces of filter body 83. As shown in FIG. 12, for example, each nozzle 125 may comprise a base engaged with extension 122, an inlet positioned in conduit 123, and an outlet directed toward the exterior surfaces of filter body 83. Coupler 121C may establish a fluid communication between conduit 123 and fluid source 24 that directs the additional cleaning fluid into conduit 123, through the inlet of each nozzle 125, and out of the outlet of each nozzle 125 toward the exterior surfaces of filter body 83.

As shown in FIG. 10, for example, outlet post 86 may comprise an open end 126, a flange 127, an extension 128, a conduit 129, and an inlet 130. Open end 126 may comprise a coupler 126C that outputs the filtered flow to treatment system 140. As shown in FIG. 12, for example, an exterior surface of extension 128 may be receivable in bearing opening 94 and bearing opening 107 along filter axis X2-X2. Flange 127 may be engaged with plate 88 to secure extension 128 in bearing opening 94 and form a watertight seal therebetween. As also shown in FIG. 12, for example, the exterior surface of extension 128 may comprise a groove 131 sized to receive a seal 132 (e.g., an O-ring) that prevents culture medium 1 from passing between the exterior surface of extension 128 and interior surfaces of bearing opening 107. Extension 128, like extension 112, may thus be securely cantilevered into the interior cavities of frame 81 and filter body 83 with flange 127. Conduit 129 may extend from open end 126 to inlet 130 through flange 127 and extension 128.

Filtration apparatus 80 may be assembled so that porous element 103 is positioned to keep plankton and suspended particles out of the interior cavity of filter body 83 when it is partially submerged in culture medium 1, allowing the filtered flow to be drawn from the interior cavity of filter body 83 through inlet 130. As shown in FIG. 9, for example, filtration apparatus 80 may be assembled by a method comprising: assembling frame 81; assembling filter body 83; locating filter body 83 in the interior cavity of frame 81; locating interior nozzle post 84 in the interior cavities of frame 81 and filter body 83; engaging interior nozzle post 84 with frame 81 and filter body 83; engaging outlet post 86 with frame 81 and filter body 83; and engaging drive element 82 with frame 81 and filter body 83.

Frame 81 may be assembled by engaging the ends of posts 89 to interior surfaces of frame plates 87 and 88. As shown in FIG. 10, for example, opposite ends of each post 89 may be engaged with plates 87 and 88 by inserting a threaded attachment element (e.g., a screw) into a threaded opening of the end opposite end through an opening in plate 87 or 88.

Filter body 83 may be assembled by engaging opposite ends of shell 102 to plates 100 and 101, engaging gear 105 with plate 100, and engaging porous element 103 with shell 102. The opposite ends of shell 102 may be secured in grooves defined by interior surfaces of plates 87 and 88. As shown in FIG. 11, for example, gear 105 may then be engaged with plate 100 by placing the interior portion of gear 105 over bearing sleeve 104 and inserting threaded attachment elements (e.g., screws) into threaded openings of plate 100 through openings in gear 105. Porous element 103 may be engaged with shell 102 by wrapping porous element 103 around shell 102 and inserting the elongated protrusions of element 103 into the elongated openings of shell 102 so that exterior surfaces of the elongated protrusions may act against interior surfaces of the elongated openings to maintain a position of porous element 103 relative to filter body 83.

Once assembled, filter body 83 may be located in the interior cavity of frame 81 so that bearing sleeve 104 and bearing opening 107 are coaxial with filter axis X2-X2. As shown in FIG. 12, for example, interior nozzle post 84 may then be located in the interior cavities of frame 81 and filter body 83 and engaged with filter body 83 by inserting extension 112 into bearing opening 92, and moving interior nozzle post 84 along filter axis X2-X2 until exterior surfaces of extension 112 are received in bearing opening 92 and flange 111 is adjacent plate 87. Interior nozzle post 84 may then be engaged with frame 81 and filter body 83 by engaging flange 111 with plate 87 so that extension 112 is securely cantilevered into frame 81 and filter body 83. The exterior surfaces of extension 112 may now provide a rotational support for interior surfaces of bearing sleeve 104, allowing one end of filter body 83 to rotate independently of frame 81. During these movements, bearing opening 92 may align extension 112 with filter axis X2-X2 so that a gap is formed between the exterior surfaces of extension 112 and the interior surfaces of bearing sleeve 104. As shown in FIG. 12, for example, seal 117 may be inserted into groove 116, prior to inserting extension 112 into bearing opening 92, to seal the gap between extension 112 and bearing sleeve 104 without preventing filter body 83 from rotating.

Exterior nozzle post 120 may be engaged with frame 81 by inserting closed end 124 through exterior nozzle post opening 109, moving closed end 124 into a position adjacent plate 88, engaging closed end 124 with plate 88 (e.g., with a threaded attachment element), and engaging threads of coupler 121C with threads of extension 122.

As shown in FIG. 12, for example, outlet post 86 may be engaged with frame 81 and filter body 83 by inserting extension 128 into bearing opening 94 and bearing opening 107, and moving extension 128 along filter axis X2-X2 until exterior surfaces of extension 128 are received in bearing opening 94 and flange 127 is adjacent plate 88. Outlet post 86 may then be engaged with frame 81 and filter body 83 by engaging flange 127 with plate 88 so that extension 128 is securely cantilevered into frame 81 and filter body 83. The exterior surfaces of extension 128 may now provide a rotational support for interior surfaces of bearing opening 107, allowing the other end of filter body 83 to rotate independently of frame 81. During these movements, bearing opening 94 may align extension 128 with filter axis X2-X2 so that a gap is formed between the exterior surfaces of extension 128 and the interior surfaces of bearing opening 107. As shown in FIG. 12, for example, seal 132 may be inserted into groove 131, prior to inserting extension 128 into bearing opening 94, to seal the gap between extension 128 and bearing opening 107 without preventing filter body 83 from rotating.

Drive element 82 may be engaged with frame 81 and filter body 83 by engaging electric motor 97 to an exterior surface of plate 87 so that the drive shaft of motor 97 extends through an opening of plate 87. As shown in FIG. 9, for example, an interior diameter of gear 98 may then be engaged with the drive shaft of motor 97 so that teeth 99 of gear 98 may be meshed with teeth 106 of gear 105, allowing gear 98 and thus filter body 83 to be rotated independently of frame 81 with electric motor 97 responsive to control signals 185 from controller 180.

Once assembled, filtration apparatus 80 may be rendered operational by a method comprising: engaging filtration apparatus 80 with culture tank 20; establishing fluid communications between one or more nozzles 85, outlet post 86, and treatment system 140; and establishing data communications between communicable elements of filtration apparatus 80 and controller 180.

Filtration apparatus 80 may be engaged with culture tank 20 so that filter axis X2-X2 is generally parallel with top surface 2 of culture medium 1. As shown in FIG. 10, for example, frame 81 may be engaged with culture tank 20 by inserting a post 28 through support openings 91 and 93 of frame plates 87 and 88; and, as shown in FIG. 1, for example, placing post 28 in the notches of supports 26 so that the weight of filtration apparatus 80 may be supported on body 21 with post 28. As shown in FIG. 1, for example, frame 81 may be adapted to keep one or more nozzles 85 out of culture medium 1 so that only a lower portion of filter body 83 may be submerged. One or more nozzles 125 may be located just above top surface 2 of culture medium 1 when the lower portion of filter body 83 is submerged.

A first fluid communication may be established between one or more nozzles 85 and fluid source 24. As shown in FIG. 2, for example, fluid source 24 may comprise a line 136 and a pump 137. Line 136 may be coupled to a pump and/or vessel operable to output the cleaning fluid to interior nozzle post 84 and exterior nozzle post 120. The first fluid communication may be established by engaging coupler 110C and 121C (e.g., FIG. 12) with line 136 (e.g., FIG. 2). Pump 137 may be located on coupler 110C and 121C or on a portion of line 136 in advance of one or more nozzles 85; and operable to control a flow rate of the cleaning fluid responsive to control signals 185 from controller 180 (e.g., FIG. 2).

A second fluid communication may be established between outlet post 86 and treatment system 140. As shown in FIG. 2, for example, treatment system 140 may comprise a line 143 positioned to output the filtered flow from filtration apparatus 80. As shown in FIG. 10, for example, the second fluid communication may be established by engaging coupler 126C with line 143.

The communicable elements of filtration apparatus 80 may comprise drive element 82, pump 137, and one or more sensors position on or about filtration apparatus 80. Data communications may be established between each communicable element and controller 180 using any known communication technologies. As shown in FIG. 2, for example, the data communications may be established by connecting drive element 82 (e.g., FIGS. 9 and 10), pump 137, and the one or more sensors to controller 180 over a wired and/or wireless network so that any control data 184 and control signals 185 may be sent and received using a communication protocol.

Once filtration apparatus 80 has been assembled and rendered operational, it may be operated to continuously output the filtered flow from outlet post 86 while intermittently rotating filter body 83 to move different areas of filter body 83 and porous element 103 into and out of culture medium 1. The intermittent rotations may be timed (manually or in response to a sensor) to limit the amount of plankton and particles that become attached to each different area of filter body 83 when the volume of culture medium 1 pass therethrough. Filter body 83 and porous element 103 may be divided into any number of different areas for this purpose. During each run time, filtration apparatus 80 may be adapted to pass volumes of culture medium 1 through each different area, remove each different area from culture medium 1 while simultaneously moving another different area into culture medium 1, and direct the cleaning fluid toward each removed area so that it is ready to be re-submerged in culture medium 1 on the next rotation of filter body 83. The second fluid communication may direct the filtered flow to treatment system 140 during each run time for further processing before being returned to culture tank 20 to replenish the volume of culture medium 1 stored therein.

Treatment System 140

Treatment system 140 may be operable to maintain the plankton population in culture medium 1 by removing toxins and/or adding oxygen to the filtered flow output from filtration apparatus 80, returning that flow back to culture tank 20 so as to replenish culture medium 1. The nutrients may comprise oxygen and/or other aquaculture supplements; and the toxins may comprise ammonia, nitrogen, and organic wastes.

Figure 25:
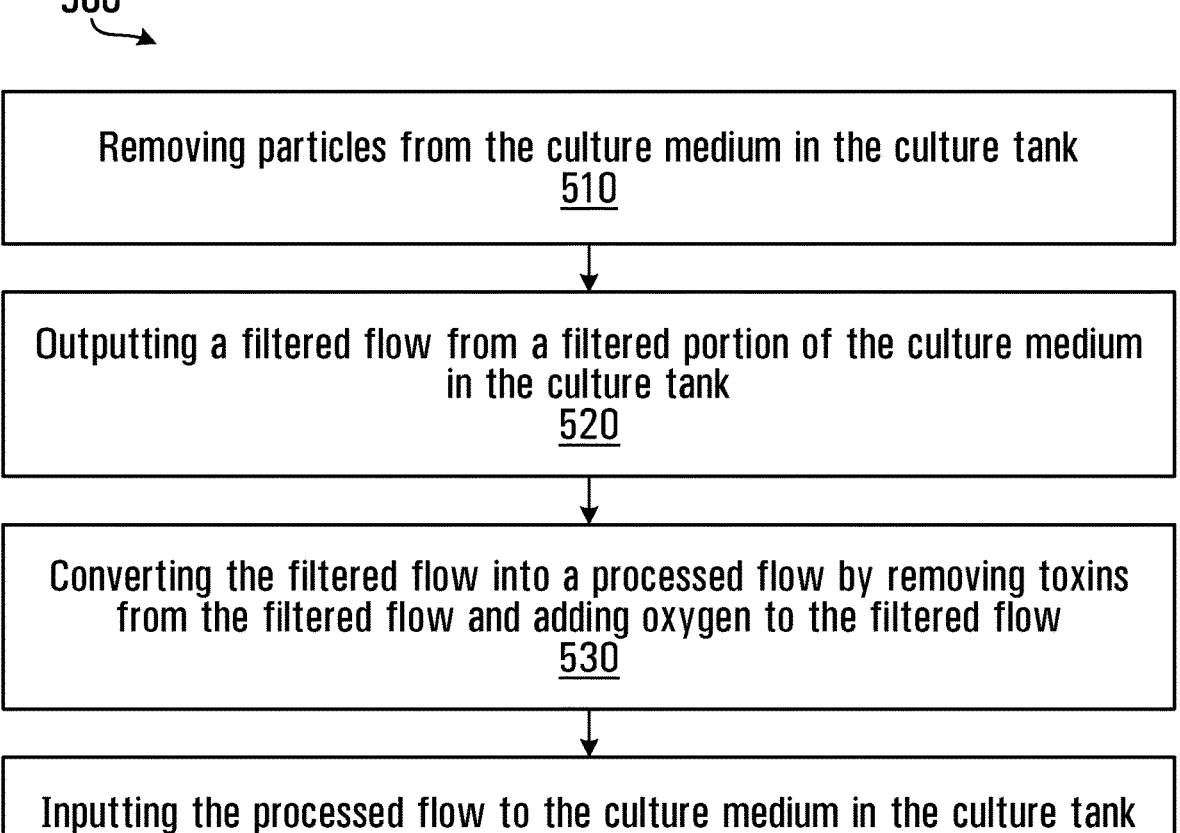
FIG. 25 depicts an exemplary method for maintaining healthy plankton populations.

As shown in FIGS. 2 and 25, for example, treatment system 140 may be operated to maintain the plankton population by performing a processing method 500 comprising: (i) removing particles from culture medium 1 (e.g., with removal apparatus 30 or other means) (510); (ii) outputting a filtered flow from a filtered portion of culture medium 1 (e.g., with filtration apparatus 80 or other means) (520); (iii) converting the filtered flow in to the processed flow by (a) removing toxins from the filtered flow, and (b) adding oxygen to the filtered flow (530); and (iv) inputting the processed flow to culture medium 1 (540). Various elements may be adapted to maintain the plankton population processing culture medium 1 according to this method. As shown in FIG. 2, for example, treatment system 140 may comprise an oxygenation loop 141 and a treatment loop 142 that are switchable between different operating modes with controller 180.

As shown in FIG. 2, for example, oxygenation loop 141 may comprise a line 143, a UV filter 144, a buffer tank 145, a line 146, a pump 147, and an oxygen cone 148. Line 143 may input the filtered flow from filtration apparatus 80 and output the filtered flow to buffer tank 145. UV filter 144 may be positioned on line 143 and operable to kill harmful bacteria in the filtered flow by exposing it to a minimum amount of UV energy. UV filter 144 may comprise one or more UV lamps operable to kill the bacteria by exposing it to a minimum amount of UV energy (e.g., approximately 40 W) for a minimum amount of time (e.g., approximately 1 to 1.5 s) while passing through line 143. As shown in FIG. 2, for example, UV filter 144 may comprise an RK2 XFL3-40L sterilizer.

Buffer tank 145 may act a passive fluid buffer for treatment system 140. As shown in FIG. 2, for example, buffer tank 145 may input different flows from oxygenation loop 141, treatment loop 142, and/or between loops 141 and 142;

and be sized to generate and/or maintain a stored volume (e.g., such approximately 150 L) of the different flows. Treatment system 140 may be operable without buffer tank 145 if required, although having a stored volume may be preferred because it buffers the flow required for other elements of system 140 and provides a convenient location to add fluids. As shown in FIG. 2, for example, buffer tank 145 may comprise a line 164 leading to a pressurized fluid source (e.g., a water supply system) and a pump 165 operable to input additional fluids to buffer tank 145 from the pressurized fluid source (e.g., a fresh supply of new water) responsive to control signals 185 from controller 180 (e.g., FIG. 2). As also shown in FIG. 2, buffer tank 145 may comprise a heater 150 and a chiller 151, both of which may be operable to modify a temperature of the stored volume in buffer tank 145 responsive to control signals 185 from controller 180.

Line 146 may output different flows from buffer tank 145 and input the flows to culture tank 20. Pump 147 may be positioned on line 146 and operable to input the different flows from buffer tank 145 and pressurize the different flows in line 146 to a desired pressure (e.g., approximately 20-35 psi). As shown in FIG. 2, for example, pump 147 may comprise a centrifugal pump e.g., an Iwaki MD-70RLTZ) that pressures the different flows before they are input to oxygen cone 148. Oxygen cone 148 may be positioned on line 146 and operable to dissolve the oxygen into the now pressurized flows in line 146. As shown in FIG. 2, for example, oxygen cone 148 may comprise a line 166 leading to a source of pressurized oxygen (e.g., a pressure vessel adjacent culture tank 20) and a valve actuator 167 operable to input the pressurized oxygen to oxygen cone 148 from the source responsive to control signals 185 from controller 180 (e.g., FIG. 2).

As shown in FIG. 2, for example, treatment loop 142 may comprise a line 154, a three-way valve 153, a line 154, a pump 155, a protein skimmer 156, a biofilter tank 157, a line 159, and a line 158. Line 152 may input different flows from buffer tank 145 and output the different flows to three-way valve 153. Three-way valve 153 may comprise three conduits and a valve actuator operable to permit treatment system 140 to be operable in different operating modes by directing the different flows through any two of the three conduits responsive to control signals 185 from controller 180 (e.g., FIG. 2). Pump 155 may be positioned on line 154 and operable to input the different flows from buffer tank 145 and pressurize the different flows in line 154 to a desired pressure (e.g., approximately 20-35 psi). Pump 155 may a centrifugal pump (e.g., another Iwaki MD-70RLTZ) that pressurizes the different flows before they are input to protein skimmer 156. Protein skimmer 156 (e.g., an RK2 5AC protein fractionator) may comprise a fluid column that removes organic wastes from the now pressured flow output from pump 155.

Biofilter tank 157 may input different flows from line 154 after removal of organic wastes therefrom; and be sized to generate and/or maintain an additional stored volume (e.g., such approximately 1,000 L) of the different flows. As shown in FIG. 1, for example, biofilter tank 157 may comprise a body, a flanged top, a conical bottom, and a frame similar to those of culture tank 20. Biofilter tank 157 may comprise bioballs, bio-media, carrier materials, and/or any similar structures comprising surface areas for housing colonies of nitrifying bacteria when submerged in the additional stored volume. In this regard, biofilter tank 157 may operable as a 'Moving Bed Biofilm Reactor.' Depending on its operating mode, three-way valve 153 may direct different flows into biofilter tank 157, where the flows will interact with the nitrifying bacteria on the bioballs and/or similar open structures to remove ammonia and nitrates. Biofilter tank 157 may modify additional characteristics of additional volume 5. As shown in FIG. 2, for example, biofilter tank 157 may comprise a heater 160 and/or a chiller 161, both of which may be operable responsive to control signals 185 from controller 180 (e.g., FIG. 2) to modify a temperature of the additional stored volume in tank 157.

Other aquaculture supplements (i.e., in addition to oxygen) may be similarly introduced to line 146 (or another line) and/or added directly to any of tanks 20, 45 and/or 157. For example, baking soda (bicarbonate), agents for neutralizing ammonia, and/or chlorine pH control (e.g. ChlorAm-X) also may be added to any of line 146, culture tank 20, buffer tank 45, and/or biofilter tank 157 as appropriate.

Because of three-way valve 153, treatment system 140 may be switched into at least three different modes, including: (i) an oxygenating mode; (ii) a cleaning mode; and (iii) a feeding mode. The oxygenating mode of treatment system 140 may be performed with oxygenating loop 141 to ensure that culture medium 1 in culture tank 20 has enough oxygen to maintain the health of a high-density plankton population. In the oxygenating mode, the filtered flow from filtration apparatus 80 may be output to line 143, passed through UV filter 144 to remove harmful bacteria, and input to buffer tank 145, where it will collect to generate a stored volume of filtered culture medium 1. Pump 147 may be operable to cause a first flow of the stored volume in buffer tank 145 to flow into line 146 independent of three-way valve 153. For example, if all three conduits of three-way valve 153 of FIG. 2 are closed, then this first flow may be circulated through oxygenation loop 141 without utilizing any elements of treatment loop 142. Alternatively, as shown in FIG. 2, for example, if an upper conduit 162 of three-way valve 153 is open and a rightmost conduit 163 of three-way valve 153 is closed, then pump 155 may be operable to cause a second flow of the stored volume in buffer tank 145 to flow into treatment loop 142 as described below with respect to the cleaning mode. Either way, pump 147 may be operated to output the first flow from buffer tank 145 and pressurize the first flow to a desired pressure (e.g., approximately 20-35 psi). The now pressurized flow may then be output with line 146 to oxygen cone 148 for mixture with a flow of pure oxygen from line 166 to increase the amount of dissolved oxygen in the flow. The oxygenated flow may then be output to culture tank 20 with line 146.

The cleaning mode of treatment system 140 may be utilized to remove toxins from an additional stored volume in biofilter tank 157. In the cleaning mode, upper portion 162 of three-way valve 153 may be open and the rightmost conduit 163 of valve 153 may be closed so that pump 155 may be operable to output a dirty flow of the additional stored volume in buffer tank 145 to line 152. The dirty flow may then pass through three-way valve 153, into line 154, through pump 155, and be pressurized therewith to obtain a desired pressure (e.g., approximately 20-35 psi) and flow rate (e.g., approximately 30 LPM). The now pressurized dirty flow may be output with line 154 to protein skimmer 156, which may remove a portion of any organic waste suspended therein and output the now skimmed dirty flow with line 154 to biofilter tank 157. The dirty flow input to biofilter tank 157 may introduce nitrogens to the additional volume stored in tank 157, and the nitrifying bacteria contained in tank 157 may be utilized to convert the nitrogens to less toxic forms, such as by converting ammonia to nitrite, and then converting the nitrite to nitrate. As shown in FIG. 2, for example, a level of the additional stored volume in biofilter tank 157 may increase relative to a flow rate of the dirty flow input thereto with line 154. Line 158 may be positioned above an overflow line for biofilter tank 157 so that the level of additional stored volume in tank 157 may be gradually increased until it exceeds the overflow line, causing a third flow to flow into buffer tank 145 with line 158. If needed to obtain a desired quality and/or flow rate of the stored volume in buffer tank 145 after the third flow is added thereto, pump 165 may be activated to introduce new water to buffer tank 145 through 164. At least a portion of the stored volume in buffer tank 145 may then be output to oxygenation loop 141.

The feeding mode of treatment system 140 may be utilized to further process the additional stored volume in biofilter tank 157 without inputting any additional fluids to culture tank 20 from oxygenation loop 142, giving the plankton time to consume food and generate organic waste. The upper portion of three-way value 151 in FIG. 2 may be closed in the feeding mode so that pump 155 may be operable to output a fourth flow of fluid from the additional stored volume in biofilter tank 157 to line 159, through three-way valve 153, into line 154, and through protein skimmer 156 for removal of organic wastes, and back into biofilter tank 157 with line 154. The additional stored volume in biofilter tank 157 may be thus continuously circulated by pump 155 and processed protein skimmer 156 and biofilter tank 157 in this matter to continuously improve its quality when system 140 is in the cleaning mode. Oxygenation loop 141 may be isolated from treatment loop 142 in this mode.

Because the oxygen levels in culture medium 1 are critical to maintaining healthy plankton populations, the oxygenating mode may be considered a default operating mode; and may be switched on continuously during operation of treatment system 140, with exception for limited maintenance periods. The cleaning mode also may be switched on most of the time to create a closed loop in which the second flow from buffer tank 145 is continually circulated with pump 155 through protein skimmer 156 and biofilter tank 157, and back into tank 145. The feeding mode may be switched on intermittently according to a feeding schedule. For example, the feeding mode may run concurrently with the oxygenating mode to continuously maintain the oxygen level of culture medium 1. Removal apparatus 30 may be operated continuously or intermittently during any of these modes to remove particles from the volume of culture medium 1 in culture tank 20. Filtration apparatus 80 also may be operated continuously or intermittently during any of these modes to output the filtered flow.

As shown in FIG. 2, for example, treatment system 140 may be operable with removal apparatus 30 and/or filtration apparatus 80, in which the stored volume in buffer tank 145 may comprise at least a portion of the filtered flow output from filtration apparatus 80. This is not required. For example, aspects of treatment system 140 also may be utilized with different variations of removal apparatus 30 and/or filtration apparatus 80, or in combination with manual methods for performing similar functions as those performed by apparatus 30 and/or 80.

To provide an example, an alternate removal apparatus (e.g., one adapted to perform a function similar to that of removal apparatus 30) may comprise a post, a porous element, and an inducer. Similar to as shown in FIG. 1 with respect to post 27, for example, end portions of the post may be inserted into the notches of supports 26 so as to engage the post with culture tank 20. The porous element may comprise a sheet of mesh material similar to porous element 65 of FIG. 6 and may likewise include openings that are sized similar to those of openings 67. The porous element may be hung over the post so that a lower portion of the porous element is submerged in culture medium 1. For example, a middle portion of the porous element may be folded over the post so the lower portion comprises two generally equal lengths of the porous element. The inducer may comprise an aerator, a pump, and/or a similar apparatus for moving flows of culture medium 1 across the lower portion of the porous element so as to push a greater volume of medium 1 through its openings. Some complexities of removal apparatus 30 may be avoided with this example, but the porous element may need to be manually removed at regular intervals (e.g., every 1-5 days), making it more labor intensive than removal device 30. Nonetheless, this example demonstrates that simpler versions of removal apparatus 30 and/or filtration apparatus 80 may be interchangeably used with treatment system 140 without departing this disclosure.

Controller 180

Controller 180 may comprise electronic components that are located proximate to system 10 (e.g., as shown in FIGS. 1 and 2) and/or remote from system 10 (e.g., in a mobile device in data communication with system 10). As shown in FIG. 2, for example, the electronic components may comprise a processor 161, a memory 182, and a transceiver 183. Processor 181 and memory 182 may comprise any computing technologies operable to input control data 184 and generate control signals 185 by executing program objects based on control data 184. Transceiver 183 may comprise any wired and/or wireless communication technologies adapted to input control data 184 from one or more input devices and/or sensors, distribute control data 184 to processor 181 and/or memory 182, receive control signals 185 generated therewith, and output control signals 185 to any communicable element of system.

With respect to removal apparatus 30, for example, control data 184 may comprise input commands from an input device (e.g., a keyboard), and the input commands may cause controller 180 to generate first control signals 185 for causing drive element 32 to rotate filter body 33 at regular intervals and second control signals 185 for causing each nozzle 34 to direct the removal fluid toward filter body 33 during and/or after each regular interval. With respect to filtration apparatus 80, for example, the input commands may cause controller 180 to generate third control signals 185 for causing drive element 82 to rotate filter body 83 at regular intervals and fourth control signals 185 for causing each nozzle 85 to direct the cleaning fluid toward filter body 83 during and/or after each regular interval. With respect to treatment system 140, for example, the input commands may cause controller 180 to generate additional control signals 185 for switching system 140 into one or more of the oxygenating, cleaning, and/or feed modes, including any signals 185 for causing activation of UV-filter 144, heater 150, chiller 151, pump 155, pump 165, heater 160, chiller 161, and/or any similar elements.

Controller 180 also may output control signals 185 to the communicable elements of system 10 in responsive to control data 184. As shown in FIG. 1, for example, system 10 may comprise one or more sensors that are positioned about removal apparatus 30, filtration apparatus 80, and/or treatment system 140 and adapted to output control data 184 associated with various quality metrics of culture medium 1, such as flow rates, temperature, nitrate levels, oxygen levels, and the like. As shown in FIG. 2, for example, each sensor may output control data 184 to transceiver 183 for distribution to processor 181 and/or memory 182, which may then utilize various program objects to generate control signals 185 responsive to control data 184.

Any of the first, second, third, and/or fourth control signals 185 described above may be generated responsive to control data 184. With respect to removal apparatus 30, for example, the one or more sensors may comprise a particle sensor (e.g., an optical sensor) that is located in culture medium 1 and adapted to output control data 184 associated with a density of the particles in medium 1; and controller 180 may comprise program objects executable by processor 181 and/or memory 182 to generate the first and second control signals 185 whenever that data 184 indicates that the density is too high. With respect to filtration apparatus 80, for example, the one or more sensors may comprise fluid level sensors that are located in any of tanks 20, 145, and/or 157 and adapted to output control data 184 associated with a depth of the fluids contained therein; and controller 180 may comprise program objects executable by processor 181 and/or memory 182 to generate the third and fourth control signals 185 whenever that data 184 indicates that the fluid levels are not sufficient.

Other control signals 185 may be similarly generated. With respect to removal apparatus 30, filtration apparatus 80, and/or treatment system 140, for example, the one or more sensors may comprise a water quality sensor adapted to output control data 184 associated with an amount of organic waste in in any of tanks 20, 145, and/or 157; and controller 180 may comprise program objects executable by processor 181 and/or memory 182 to generate additional control signals 185 for activating apparatus 30, activating apparatus 80, and/or switching system 140 into the cleaning and/or feeding modes and activating any element associated therewith, such as three-way valve 153, buffer tank 145, and/or pump 155. As a further example, treatment system 140 also may comprise temperature sensors adapted to output control data 184 associated with a temperature of any fluid described above; and controller 180 may comprise program objects executable by processor 181 and/or memory 182 to generate additional control signals 185 for causing any of chiller 151, heater 150, chiller 161, and/or heater 160 to modify a temperature of such fluids when that control data 184 indicates that the temperature is outside of a predetermined operating range.

In keeping with above, controller 180 may be operable to control any element of system 10 based on any sensory data to realize any type of closed-loop control strategies without departing from this disclosure. The program objects may be utilized to realize any such strategies and determine priorities therebetween, allowing any elements of system 10 to be responsively controlled. For example, regardless of the operating mode of treatment system 140, if porous element 103 becomes clogged, then the filtered flow output from filtration apparatus 80 will decrease, causing a fluid level in culture tank 20 to increase until a sensor located in tank 20 starts outputting control data 184 that, by way of controller 180, activates nozzles 85 and/or 125 until control data 184 indicates that the fluid level in tank 20 has returned to normal. Countless such examples may be realized with system 10 according to the examples described herein, each possible combination and iteration being part of this disclosure.

System 210

Figure 13:
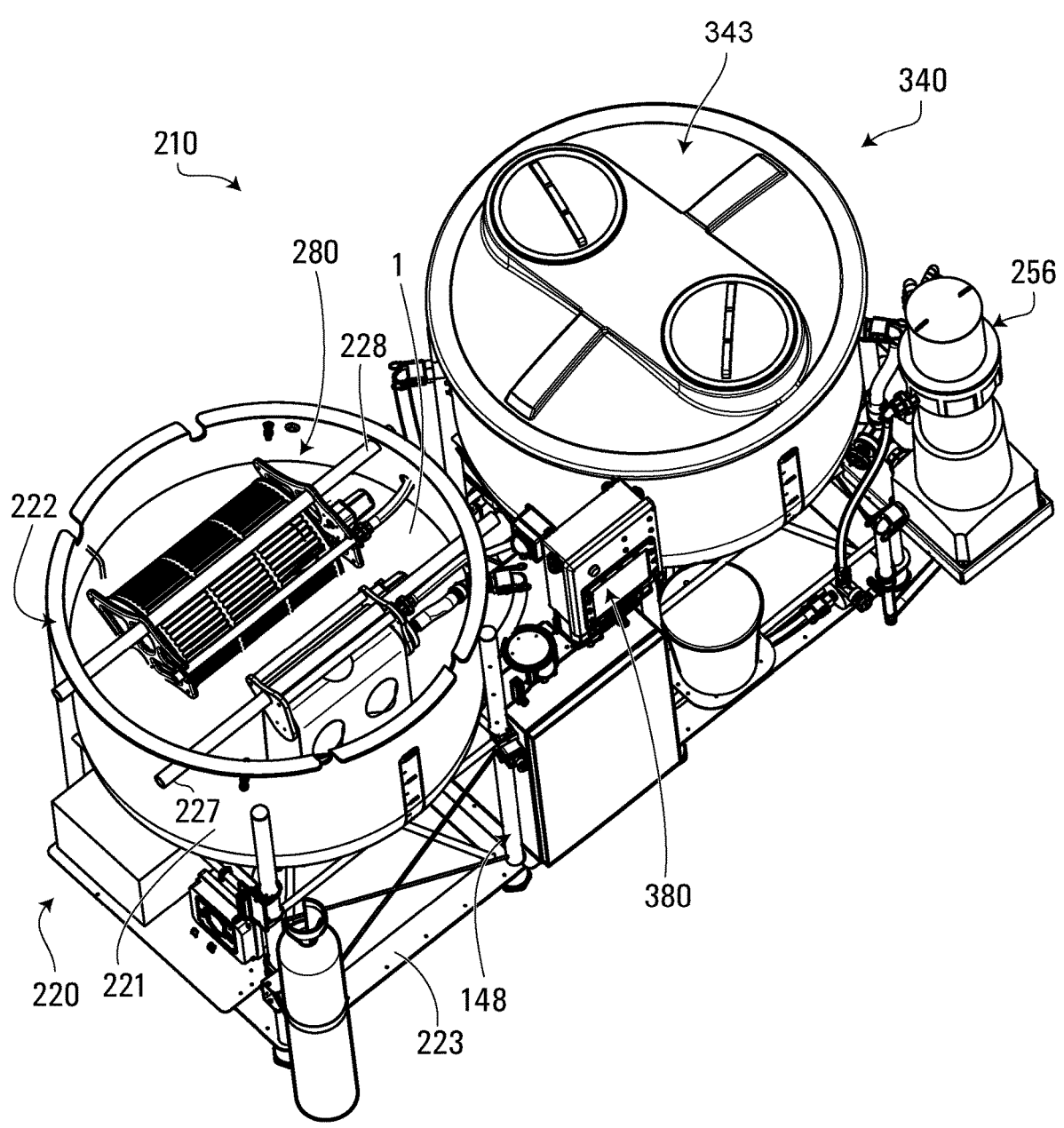
FIG. 13 depicts a perspective view of an exemplary system for maintaining healthy plankton populations.

Additional aspects of this disclosure are now described with reference to an exemplary system 210 for maintaining healthy plankton populations in a culture medium 1, such as fresh water, saltwater, and anything added thereto. Aspects of system 210 may be similar or identical to aspects of system 10, but within the 200 or 300 series of numbers. A number of exemplary differences are now described in detail with reference to FIGS. 13-22, any combination of which may be utilized with system 10 and vice versa. As shown in FIG. 13, for example, system 210 may comprise: a culture tank 220; a removal apparatus 230; a filtration apparatus 280; a treatment system 340; and a controller 380.

Culture tank 220 may comprise a free-standing vessel composed of any metallic and/or polymeric material suitable for containing a volume of a culture medium 1. Culture tank 220 of FIGS. 13 and 14 may be similar or identical to culture tank 20 described above. Filtration apparatus 280 may be similar or identical to filtration apparatus 80 described. And controller 280 may be similar or identical to controller 180 described above.

Figure 22:
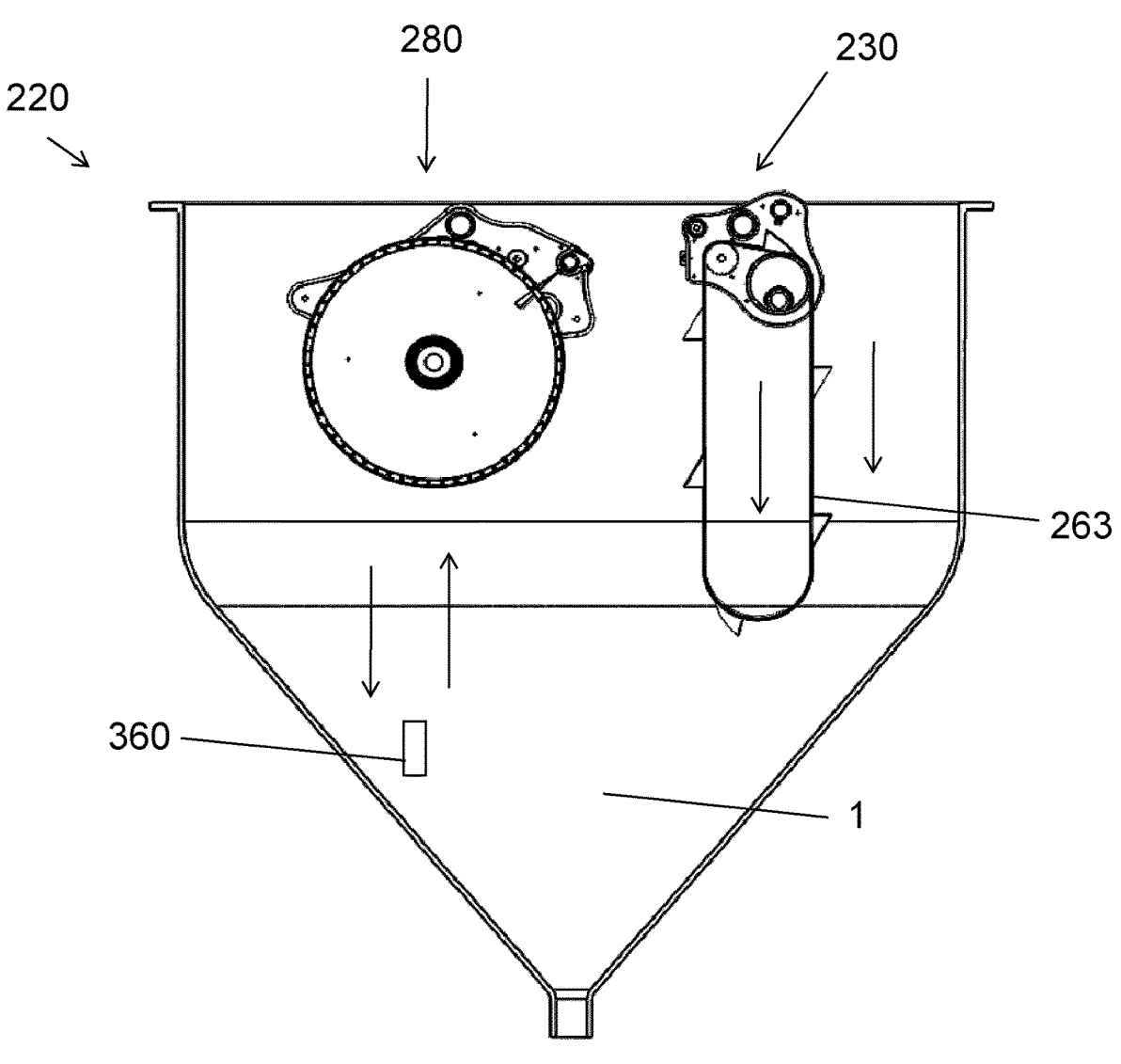
FIG. 22 depicts an operational section view of the FIG. 13 system.

An exemplary layout of system 210 is shown in FIG. 13, which shows filtration apparatus 80 at left and removal apparatus 230 at right. As shown in FIG. 22, an air diffuser may be placed on the left side of culture tank 220, beneath filtration apparatus 80, to help induce a convective flow that rises under filtration apparatus 80 and drops on the right side at removal apparatus 230. The convective flow causes culture medium 1, and thus particles, to move down through filters of a filter body of removal apparatus 280, allowing the particles to be captured with the filters. When actuated by controller 180, removal apparatus 230 may rotate the filter body in a counterclockwise direction (from viewpoint of FIG. 13) to lift the filters out of culture medium 1 along with the captured particles. A first portion of the lifted particles may fall into an opening of a conduit with gravity forces once the filters are positioned over the opening. A cleaning fluid may be sprayed onto the filter body as it moves across the opening, moving a second portion of the lifted particles away from the filters and into the conduit and generating an effluent flow that is directed away from culture medium 1 in culture tank 220 with the conduit.

Removal Apparatus 230

Removal apparatus 230, similar to removal apparatus 30, may output an effluent flow comprising particles that have been lifted out of culture medium 1 (the "effluent flow"). The particles may comprise uneaten rotifer food, decomposing matter, and the like. In contrast to apparatus 30, removal apparatus 230 may be described as a "belt filter" device, in which a filter body is suspended in culture tank 220 and operated constantly or intermittently to remove large and suspended particles from culture medium 1. During operation of removal apparatus 230, a filter of the filter body may be rotated through culture medium 1 to: collect particulate; lift the filter out of culture medium 1; position the filter relative to a conduit so that a first portion of the lifted particles fall into the conduit with gravity forces; and position the filter relative to flow of removal fluid so that a second portion of the lifted particles are moved off the filter and into the conduit with impact forces applied by the removal fluid. As with apparatus 30, the effluent flow may comprise the first and second portions of the lifted particles and a portion of the removal fluid.

As shown in FIGS. 13-21, for example, removal apparatus 230 may comprise: a frame 231, a drive element 232, a filter body 263, and one or more nozzles 234. With these exemplary elements, removal apparatus 230 may be operable to maintain a plankton population in a culture medium by removing particles from the culture medium in a manner similar to that of removal apparatus 30.

Figure 15:
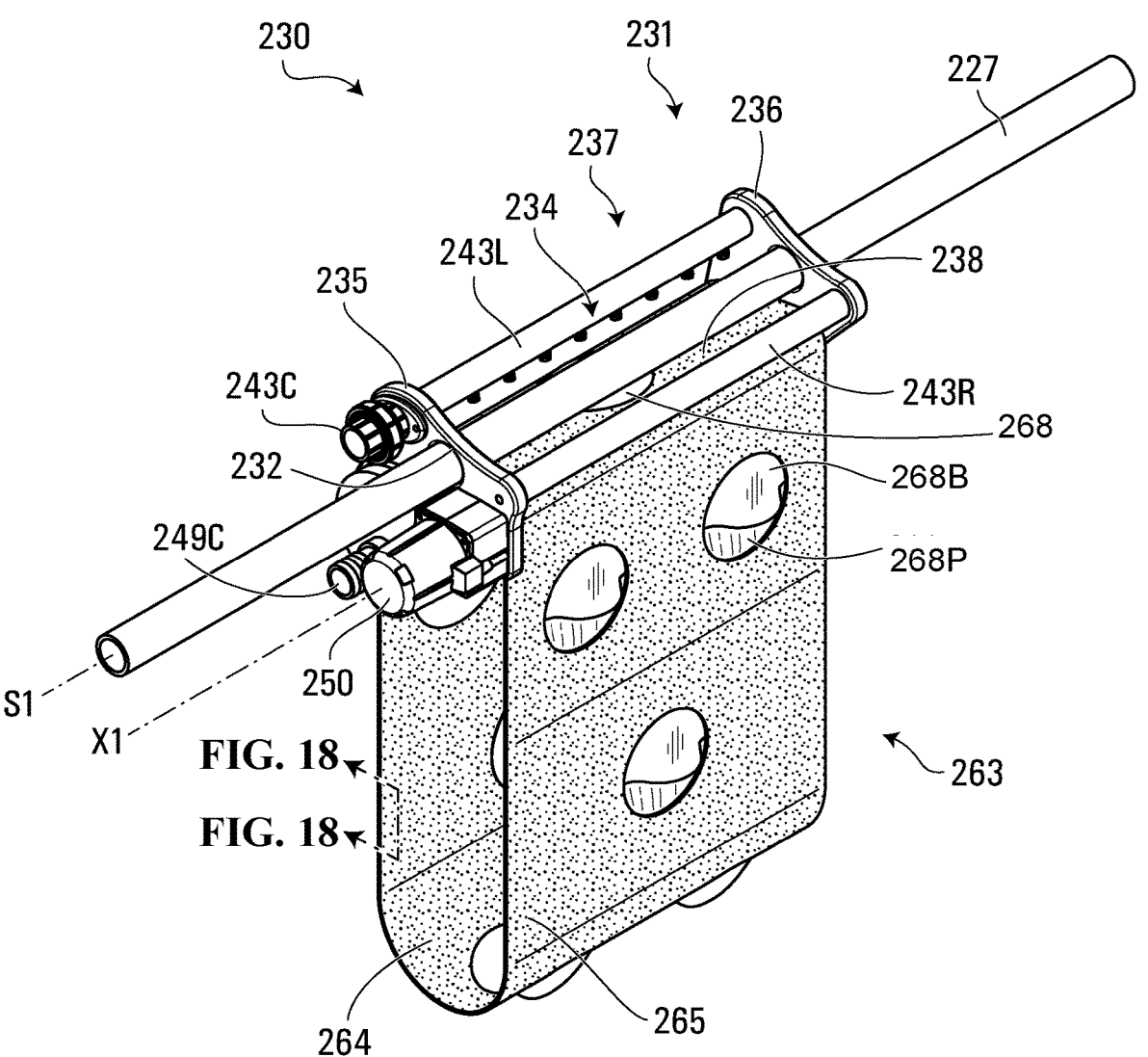
FIG. 15 depicts an exemplary apparatus for maintaining healthy plankton populations.

As shown in FIGS. 15 and 22, for example, removal apparatus 230 may be similarly operated to maintain a plankton population in culture medium 1 by removing particles from culture medium 1 according to a method (e.g., similar to method 400) comprising: (i) rotating filter body 263 to (a) lift the particles from culture medium 1 with a filter of filter body 263, and (b) position the filter relative to a conduit so that a first portion of the lifted particles fall into the conduit; (ii) directing a removal fluid toward filter body 263 to move a second portion of the lifted particles off the filter and into the conduit with impact forces applied by the removal fluid; and (iii) outputting an effluent flow from the conduit, the effluent flow comprising the first and second portions of the lifted particles and a portion of the removal fluid. Various aspects of removal apparatus 230 may be thus adapted to maintain the plankton population in culture medium 1 by removing particles from culture medium 1 according to this method.

Much like frame 31 of system 10, frame 231 of system 210 may engage removal apparatus 230 with culture tank 220. As shown in FIG. 15, for example, frame 231 may comprise a plate 235, a plate 236, a post 243L, a post 243R, and a trough post 238.

Plate 235 may comprise openings extending therethrough to receive a first end of post 243L, first end of a post 227, and a first end of trough 238. Interior surfaces of plate 235 may be engaged with a first end of post 243R. Plate 236 may comprise interior surfaces engageable with a second end of post 243R, a second end of post 227, and a second end of trough 238. Plate 236 also may comprise an opening extending therethrough to receive a second end of post 227. As shown in FIG. 15, for example, posts 243L, 243R, and 238 may be engaged with plates 235 and 236 to form a rigid structure with an interior cavity. Posts 243L, 243R, and 238 may serve as beam elements spanning between plates 235 and 236. The beam elements may resist deflections caused by drag forces associated with culture medium 1, gravity forces associated with a weight of filter panel 263 and any suspended particles being lifted therewith, and impact forces associated with the removal fluid. When this rigid structure is formed, post 227 may extend through removal apparatus 230 along a support axis S1-S1, allowing for attachment to culture tank 220 in manner similar to apparatus 30.

Figure 16:
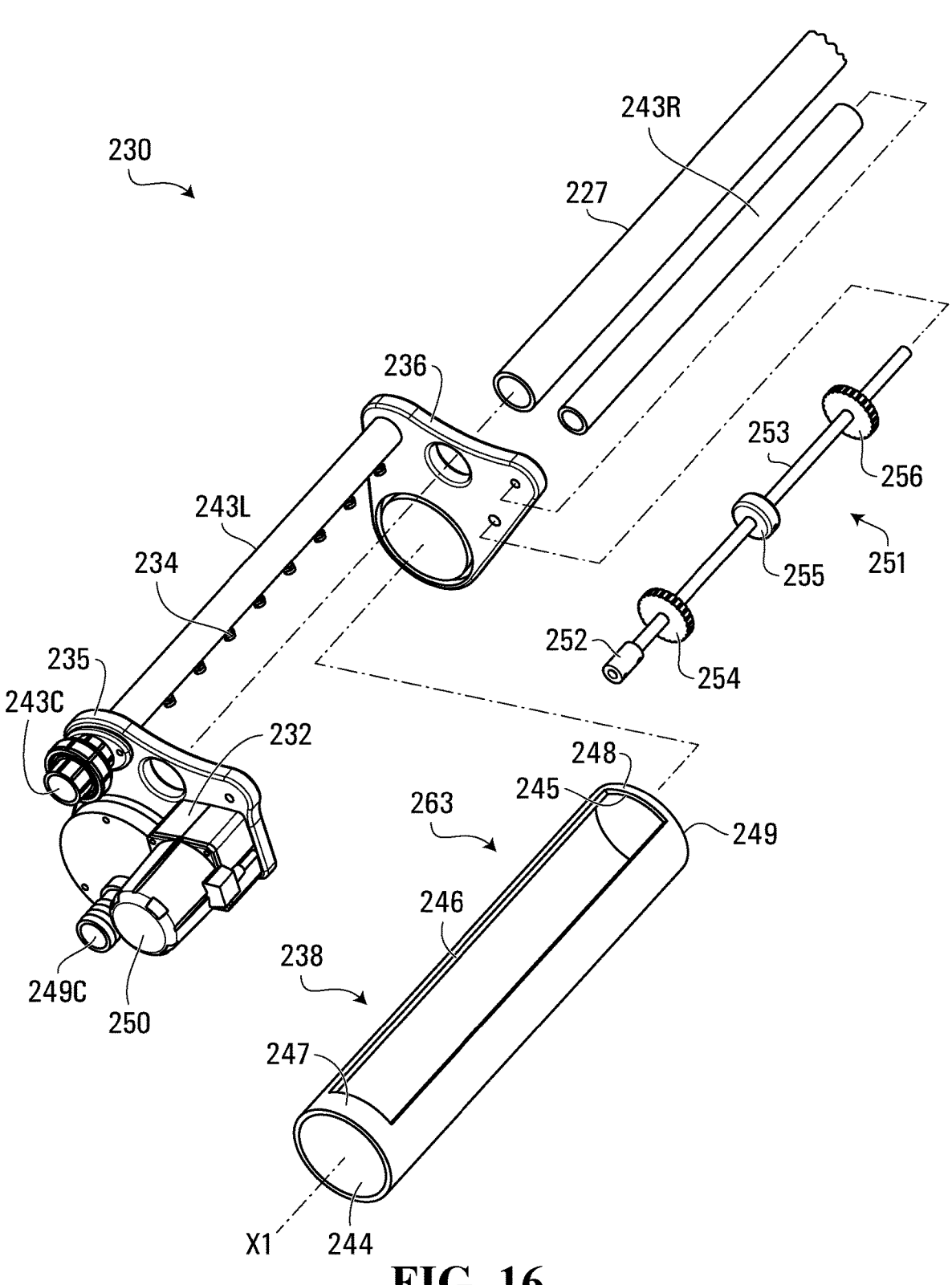
FIG. 16 depicts an exploded view of the FIG. 15 apparatus.
Figure 21:
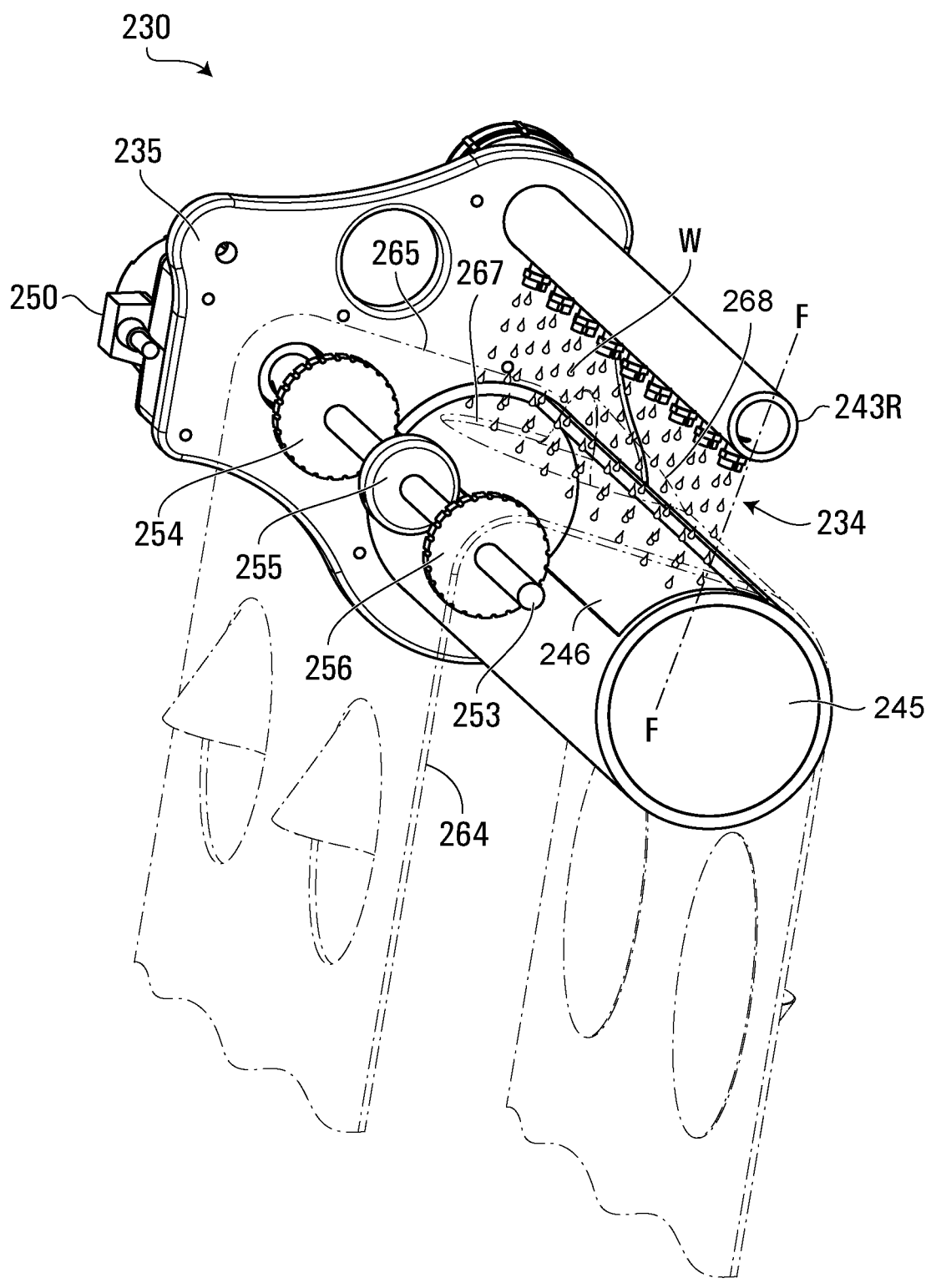
FIG. 21 depicts an operational section view of the FIG. 15 apparatus and FIG. 18 filter body.

One or more nozzles 234 may be located on post 243L. As shown in FIG. 15, for example, post 243L may comprise a tube wall extending between frame plates 235 and 236, and a conduit extending through the tube wall. Each nozzle 234 may comprise a base engaged with the tube wall, an inlet positioned in the conduit, and an outlet directed toward the interior cavity of frame 231. As shown in FIG. 21, for example, each outlet of each nozzle 234 may direct a removal fluid W toward the interior cavity of frame 231 along a different flow path F-F. Removal fluid W may comprise any combination of water, air, and/or other agent deliverable with fluid source 224 (e.g., FIG. 13). As shown in FIG. 16, for example, the first end of post 243L may be closed and adjacent plate 236; the second end of post 243L may be open and extend through plate 235 and comprise a coupler 243C adapted to input the removal fluid from fluid source 224.

Outlet post 238 may output the effluent flow to a disposal system. As shown in FIG. 16, for example, outlet post 238 may comprise an open end 244, a conduit 245, an input opening 246, a bearing surface 247, a bearing surface 248, and a closed end 249. Conduit 245 may extend between open end 244 and closed end 249. Input opening 246 may extend into conduit 245 through an upper portion of outlet post 238 located between its bearing surfaces 247 and 248. As shown in FIG. 16, for example, input opening 246 may

Figure 14:
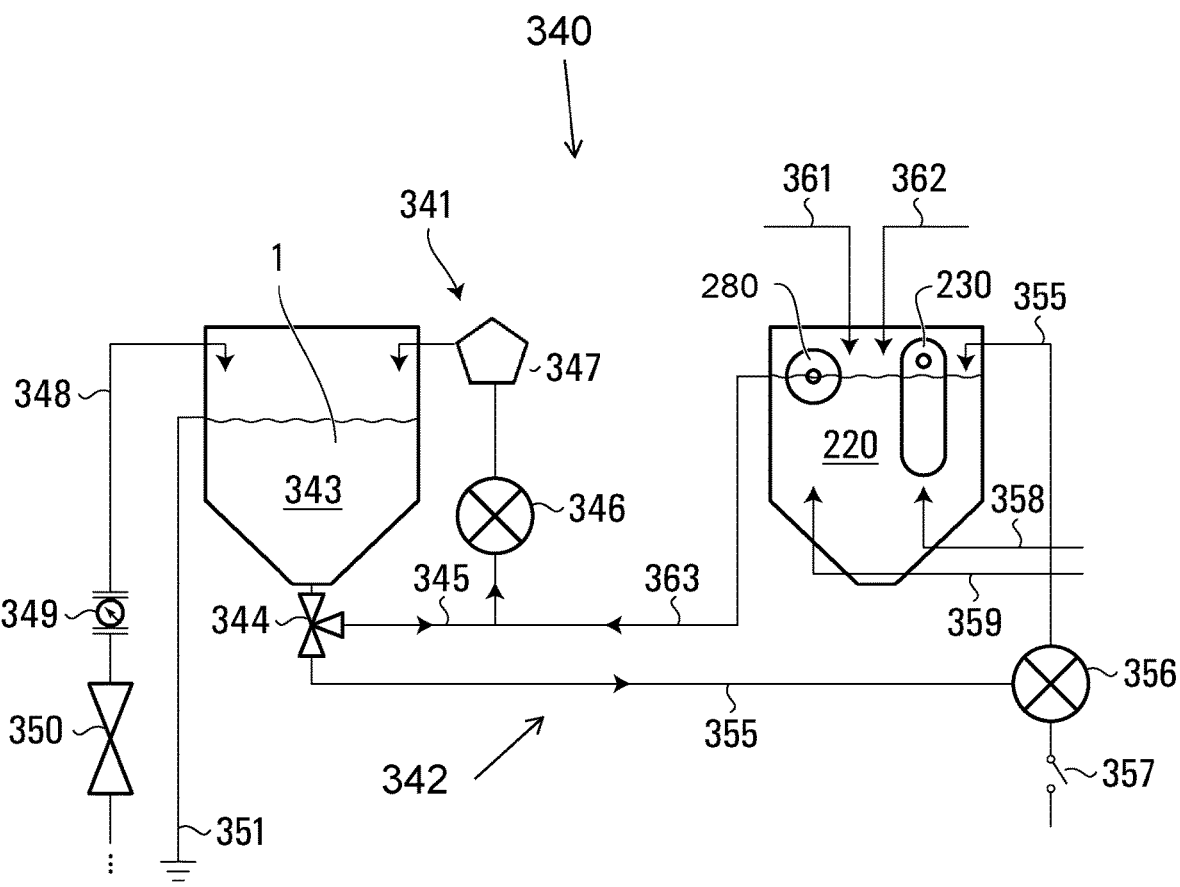
FIG. 14 depicts a flow diagram for the FIG. 13 system.

31 comprise an elongated opening with a cross-sectional area that extends along filter axis X1-X1 and is oriented towards one or more nozzles 234 to capture as much of the effluent flow as possible. As shown in FIGS. 14 and 15, for example, open end 244 may comprise a coupler 249C adapted to establish a fluid communication with a disposal system, such as a floor drain.

Drive element 232 may rotate filter body 263 to lift the particles from the culture medium with a filter of filter body 263 and position the filter relative to conduit 245 so that a first portion of the lifted particles fall into conduit 245. As shown in FIG. 16, drive element 232 may comprise an electric motor 250 and a drive shaft 251. As shown in FIG. 15, for example, electric motor 250 may be engaged with exterior surfaces of plate 235 and comprise an output shaft extending through an opening of plate 235 when mounted thereto. Electric motor 250 may rotate the output shaft relative to plate 235 responsive to control signals 185 from controller 180 (e.g., FIG. 2). As shown in FIG. 16, for example, drive shaft 251 may comprise a coupler 252, a drive shaft body 253, a drive gear 254, a guide element 255, and a drive gear 256. Coupler 252 may be located at a first end of drive shaft 251 and engageable with the output shaft of electric motor 250. A second end of drive shaft 251 may be receivable in an opening extending into and/or a rotational mount attached to the interior surfaces of plate 236. Drive gears 254 and 256 may be rotatable with drive shaft body 253 and comprise teeth engageable with filter body 263 described below. Guide element 255 may be rotatable with drive shaft body 253 and comprise bearing surfaces that interact with a central portion of filter body 263 to keep it from sagging between gears 254 and 256.

In contrast to filter body 63 of removal apparatus 30, filter body 263 of removal apparatus 230 may comprise a belt having a plurality of different material types and/or layers. The belt may be a long, wide belt (19" wide, 60" long) made from two or more different layers. As shown in FIG. 15, for example, filter body 263 may comprise a structural layer 264 and a filter layer 265. Structural layer 264 and/or filter layer 265 may be optimized for weight and rigidity to increase the efficiency of removal apparatus 230, and for optimal positioning of filter layer 265 relative to culture medium 1 and/or one or more nozzles 234.

Figure 19:
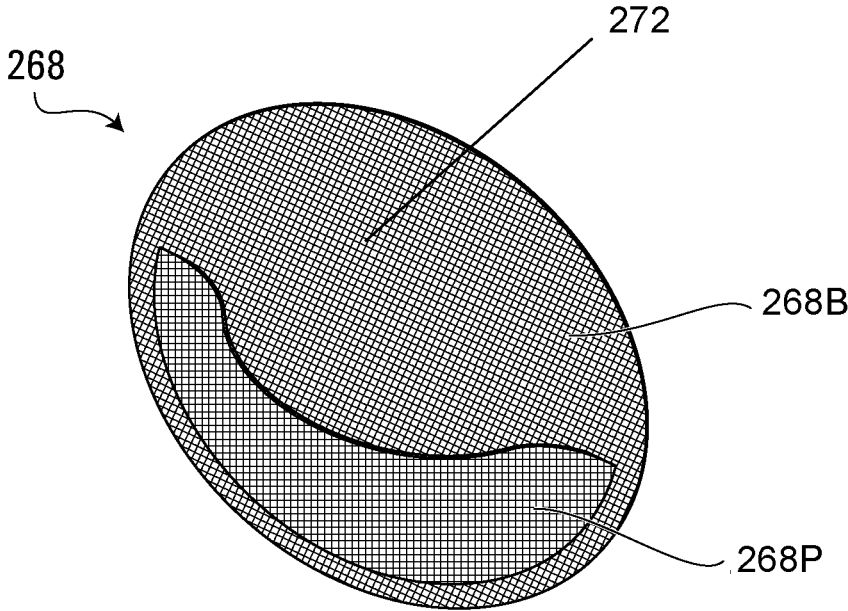
FIG. 19 depicts a first side view of the FIG. 15 apparatus and FIG. 18 filter body.

Structural layer 264 may comprise a flexible sheet of interlinked elements that are engageable with gears 254 and 256 to rotate filter body 263 around outlet post 238 and drive shaft 251. As shown in FIG. 19, for example, structural layer 264 may comprise a structural layer made from stainless steel wire with openings and/or surfaces that are engageable with teeth of gears 254 and 256. The interlinked elements may comprise any type of metallic and/or polymeric elements (e.g., bent wires) that are formed together, interwoven, and/or otherwise linked to form interior surfaces of filter body 263. To provide a particular example, structural layer 264 may comprise a conveyor belt material made of a food grade material, like stainless steel, such as those currently used in some toaster ovens. As also shown in FIG. 19, for example, structural layer 264 may comprise a first porosity defined by spaces between the interlinked elements.

Figure 17:
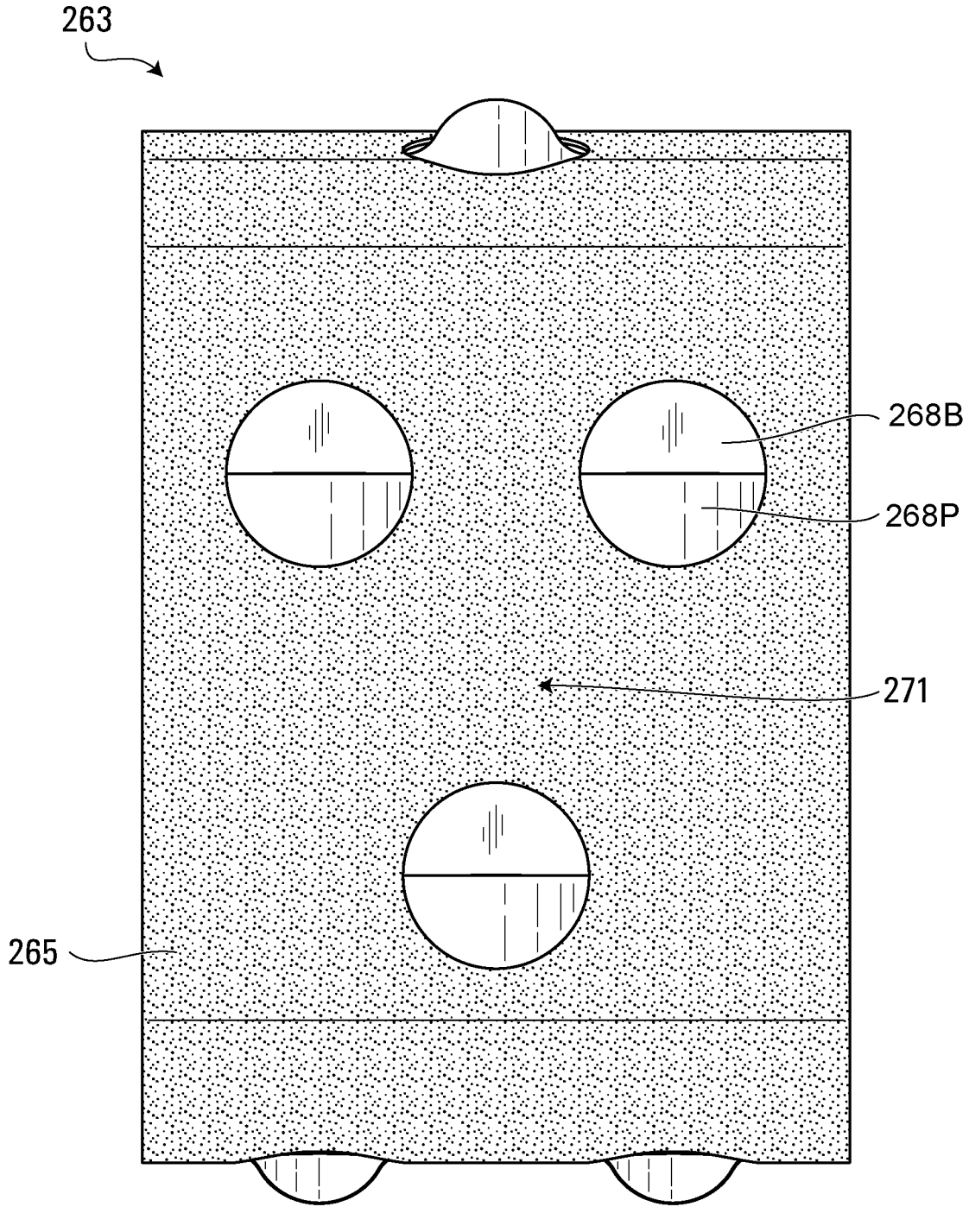
FIG. 17 depicts a driveshaft for the FIG. 15 apparatus.

Filter layer 265 may comprise a flexible sheet of filtering mesh. As shown in FIG. 17, for example, filter layer 265 may comprise a plurality of polymeric strands that are formed and/or interwoven together to form exterior surfaces of filter body 263. Filter layer 265 may comprise a high surface area spongy nylon mesh (about 0.375" thick, uncompressed) that serves as a filter for removing particles from culture medium 1. Similar to porous element 103 of removal

Figure 18:
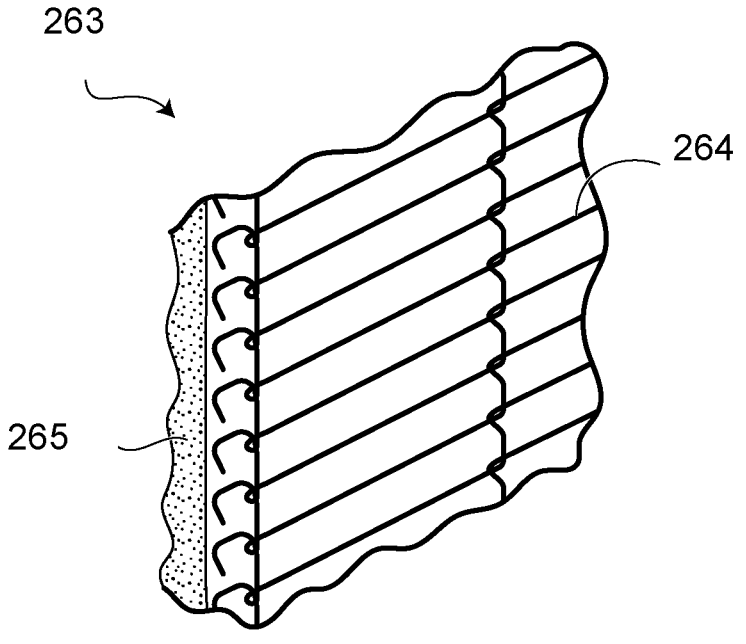
FIG. 18 depicts a filter body of the FIG. 15 apparatus.

32 apparatus 80, filter layer 265 may surround and wrap around structural layer 264, spanning between its openings. For example, filter layer 265 may similarly comprise a sponge-like material that defines openings 271 and comprises a web or matrix of fibers that are formed and/or woven together so that each opening 271 has an irregular 3D shape, some of which may allow plankton to pass through. When its openings 271 are sized accordingly and unclogged, the internal surface areas of filter layer 265 may capture fine particles in culture medium 1 while simultaneously allowing flows of culture medium 1 to pass through. As shown in FIG. 18, for example, filter layer 265 may comprise a second porosity defined by openings 271, and the first porosity of structural layer 264 may be greater than the second porosity of filter layer 265.

As shown in FIG. 15, for example, filter layer 265 of filter body 238 may be rotatable with drive element 232 to lift particles out of culture medium 1 and allow a first portion of the lifted particles to fall into conduit 245; and operable with one or more nozzles 234 to move a second portion of the lifted particles off the filter and into the conduit with impact forces applied to filter layer 265 by the removal fluid. Because it is made from denser materials, structural layer 254 may support filter layer 265 when impact forces are applied thereto by the removal fluid output from one or more nozzles 234, add mass that prevents filter layer 265 from floating in culture medium 1, and prevent filter layer 265 from stretching. As shown in FIG. 16, for example, backing layer 264 may be engaged with filter layer 265 at spaced apart locations so that the cylindrical shape of filter body 263 is defined by layers 264 and 265. Filter body 263 may thus be described as a flexible, multi-layered sheet of material having a first layer (e.g., structural layer 264) with a first porosity and a second layer (e.g., filter layer 265) having a second porosity that is greater than the first porosity and operable to remove particles from culture medium 1.

Similar to filter body 63 of removal apparatus 30, filter body 263 of removal apparatus 230 may comprise structural features that aid its ability to 'scoop' particles out of culture medium 1 when moved therethrough by drive element 232. As shown in FIGS. 15, 16, and 17, filter layer 265 of filter body 263 may comprise a plurality of openings 267 and a plurality of pockets 268. Each opening 267 may comprise a geometric shape (e.g., circular) that extends through filter layer 265 to expose backing layer 264 when layers 264 and 265 are engaged with one another.

Each pocket 268 may comprise a porous material that has been formed or printed into a 3D filtering shape including a scooping portion that may be contained in one of openings 266 and engaged with filter layer 265. Much like porous element 65 of removal apparatus 30, porous material forming pocket 268 may comprise a grid with openings 272 sized to lift suspended particles of a certain size from culture medium 1 while allowing flows of culture medium 1 to pass through. A mesh material, a fibrous pad, or a similar structure may be used to define the grid. Each opening 272 may comprise a maximum width larger than some of the plankton (e.g., most rotifers), such as a maximum width of approximately 0.5 mm or greater, or between approximately 0.5 mm and approximately 1.0 mm, or less than approximately 2.0 mm. Pockets 268 may comprise one or more layers of any filtering materials. For example, each pocket 268 and/or any portion thereof may comprise a first layer of nylon mesh having openings 272 with a maximum width of approximately 0.5 mm, a second layer of nylon mesh having openings 272 with a maximum width of approximately 1.5 mm, and/or a third layer of nylon mesh having openings 272 with a maximum width of approximately 0.5 mm. When its openings 272 are sized accordingly, each pocket 268 may thus be adapted to lift any suspended particles having a width greater that the maximum width of its openings 272, such as uneaten portions of plankton food, while minimizing the amount of plankton lifted therewith. Smaller openings 272 may be used to remove some of the plankton. As also shown in FIG. 19, for example, the porous material forming each pocket 268 may comprise a third porosity defined by spaces in between openings 272.

As shown in FIG. 19, for example, each pocket 268 may comprise a protruding portion 268P and a backing portion 268BB that is formed or printed from the porous material. Protruding portion 268P may comprise a semi-circular shape with a curved edge and a straight edge. Backing portion 268B may comprise a circular sheet. As shown in FIG. 19, for example, the 3D filtering shape may be formed by folding the straight edge of portion 268P, placing the curved edge of portion 268P against a front surface of backing portion 268B, and engaging the curved edge with backing portion 268B (e.g., fused, glued, sewn, etc.) to maintain a radius of the fold and provide pocket 268 with a conical shape. Similar structures may be formed with 3D printing or another additive manufacturing method. Each pocket 268 may be contained in one of openings 266 by engaging a perimeter of the front surface of backing portion 268B to the back surface of filter layer 265 so that protruding portion 268P extends outwardly from backing portion 268B and through the one opening 266.

The three-dimensional filtering shape of each pocket 268 may be resiliently deformable between:

an open configuration, in which the scooping portion extends outwardly from backing portion 268B; and a deformed configuration, in which some parts of the scooping portion have been moved toward backing portion 268B by external forces. A flexibility of pocket 268 may be optimized (e.g., by increasing a diameter of fibers of the mesh material) so that the conical shape is biased outward and thus operable to stay open when filter body 263 is rotated through culture medium 1, impacted by the cleaning fluid, and/or otherwise deformed. A number of benefits may be realized by adding at least one pocket 268 to filter body 263. For example, because of its three-dimensional shape and porosity, each pocket 268 may be uniquely configured to capture and remove large, dense particles from culture medium 1, some of which might tend to clog or otherwise not attach to filter layer 264. Filter layer 265 may be more effective than pockets 268 at capturing small floating particles, but harder to clean, making large particles likely to clog the mesh; whereas pockets 268 may be less effective at capturing small floating particles but easier to clean because large particles typically don not clog the mesh. Pockets 268 also may be required capture some particles, including any large particles that don't attach as readily to the spongy mesh. For example, the third porosity of pockets 268 may be larger than the second porosity of filter layer 265 and yet smaller than the first porosity of structural layer 264.

Removal apparatus 230 may be assembled to provide a stable rotational platform for drive shaft 251 and maintain an alignment between one or more nozzles 234 and input opening 246. As shown in FIGS. 16, for example, removal apparatus 230 may be assembled by a method comprising: partially assembling frame 231; locating filter body 263 between plates 235 and 236; engaging outlet post 238 with frame 231; and engaging drive element 232 with frame 231 and filter body 263.

Frame 231 may be partially assembled by engaging opposite ends of posts 243L and 243R with interior surfaces of plates 235 and 236. As shown in FIG. 15, for example, the second ends of posts 243L and 243R and the first end of post 243R may be engaged with the interior surfaces of plates 235 and 236 by inserting a threaded attachment element (e.g., a screw) into a threaded opening of each second or first end through an opening in plate 235 or 236. The first end of post 243L may be inserted through the opening extending through plate 235 and comprise exterior threads that are engageable with interior threads of coupler 243C. The interaction of these threads may be used to apply tensile forces to plates 235 and 236 that enhance the rigidity and stiffness of frame 231.

Filter body 263 may be located between plates 235 and 236 so that the interior of filter body 263 is located between the openings extending through plates 235 and 236 to receiving outlet post 238. Assembly instructions for filter body 263 itself are provided above.

Outlet post 238 may be engaged with frame 231 by inserting open end 344 into the opening extending through frame 236, moving open end 244 towards plate 235 until it passes through the interior of filter body 263 and enters the opening extending through plate 235. Open end 344 may be inserted through the opening extending through plate 235 and comprise exterior threads that are engageable with interior threads of coupler 249C. As shown in FIG. 16, for example, additional threaded connections may be established between coupler 249C and the exterior of plate 235. The interaction of these threads also may apply forces to plates 235 and 236 that further enhance the rigidity and stiffness of frame 231. As shown in FIG. 16, for example, outlet post 238 may extend between plates 235 and 236 so that any suspended particles directed into input opening 246 may flow into conduit 245 and out of closed end 244 along filter axis X1-X1 while filter body 263 is rotated. Coupler 249C may then direct the suspect particles into the waste disposal system.

As shown in FIG. 16, for example, drive element 232 may be engaged with frame 231 and filter body 33 by engaging electric motor 250 to an exterior surface of plate 235 so that the drive shaft of motor 250 extends through an opening extending through plate 236. As also shown in FIG. 16, for example, drive shaft 251 may be located in the interior of filter body 263 and positioned to fixedly engage the first end of drive shaft 251 with the output shaft and the rotatably engage the second end of drive shaft 251 with the opening extending into and/or rotational mount of plate 236, allowing drive shaft 251 to rotate independently of frame 231 with electric motor 250 responsive to control signals 185 from controller 180 (e.g., FIG. 2). At this point, the teeth of gears 254 and 256 may be received in spaces between the interlinked elements of structural layer 264 and thus operable transfer rotational forces thereto. The bearing surfaces of guide element 255 also may be in contact with interior surfaces of structural layer 264.

In keeping with above, once removal apparatus 230 has been assembled, it may be rendered operational by a method comprising: mounting removal apparatus 230 to culture tank 220; establishing fluid communications between culture tank 220, one or more nozzles 234, outlet post 238, and treatment system 140 (described above) or 340 (described below); and establishing data communications between communicable elements of removal apparatus 230 and controller 180.

Removal apparatus 230 may be engaged with culture tank 220 to prevent culture medium 1 from flowing into the waste disposal system, and to limit biofouling by minimizing a surface area of filter body 263 in culture medium 1 at any time. As shown in FIG. 16, for example, frame 231 may be engaged with culture tank 220 by inserting post 227 through the openings extending through plates 235 and 236 and a corresponding set of openings extending through the sidewalls of tank 220 so that the weight of removal apparatus 230 may be supported on tank 220 with posts 27. As shown in FIG. 15, for example, frame 231 may be adapted to keep outlet post 238 out of culture medium 1 so that only a lower portion of filter body 263 may be submerged in the culture medium at any one time to limit biofouling.

A first fluid communication may be established between one or more nozzles 234 and a fluid source, such as fluid source 24 described above. As shown in FIG. 2, for example, fluid source 24 may comprise line 133 and pump 134. Line 133 may be coupled to a pump and/or vessel operable to output the removal fluid to one or more nozzles 234 at a desired pressure (e.g., approximately 30-70 psi). The first fluid communication may be established by engaging coupler 243C (e.g., FIG. 4) with line 133 (e.g., FIG. 2). Pump 134 may be located on coupler 243C and/or on a portion of line 133 in advance of one or more nozzles 234; and operable to control a flow rate of the removal fluid responsive to control signals 185 from controller 180 (e.g., FIG. 2).

A second fluid communication may be established between outlet post 238 and the disposal system, such as the aforementioned floor drain. As shown in FIG. 15, for example, the second fluid communication may be established by engaging coupler 249C with line that directs the effluent flow into the disposal system.

The communicable elements of removal apparatus 230 may comprise drive element 232 and one or more sensors positioned on or about apparatus 230. As described above and shown in FIG. 2, data communications may be established between each controllable element and controller 180 using any known communication technologies so that any control data 184 and control signals 185 may be sent and received using a communication protocol.

Figure 20:
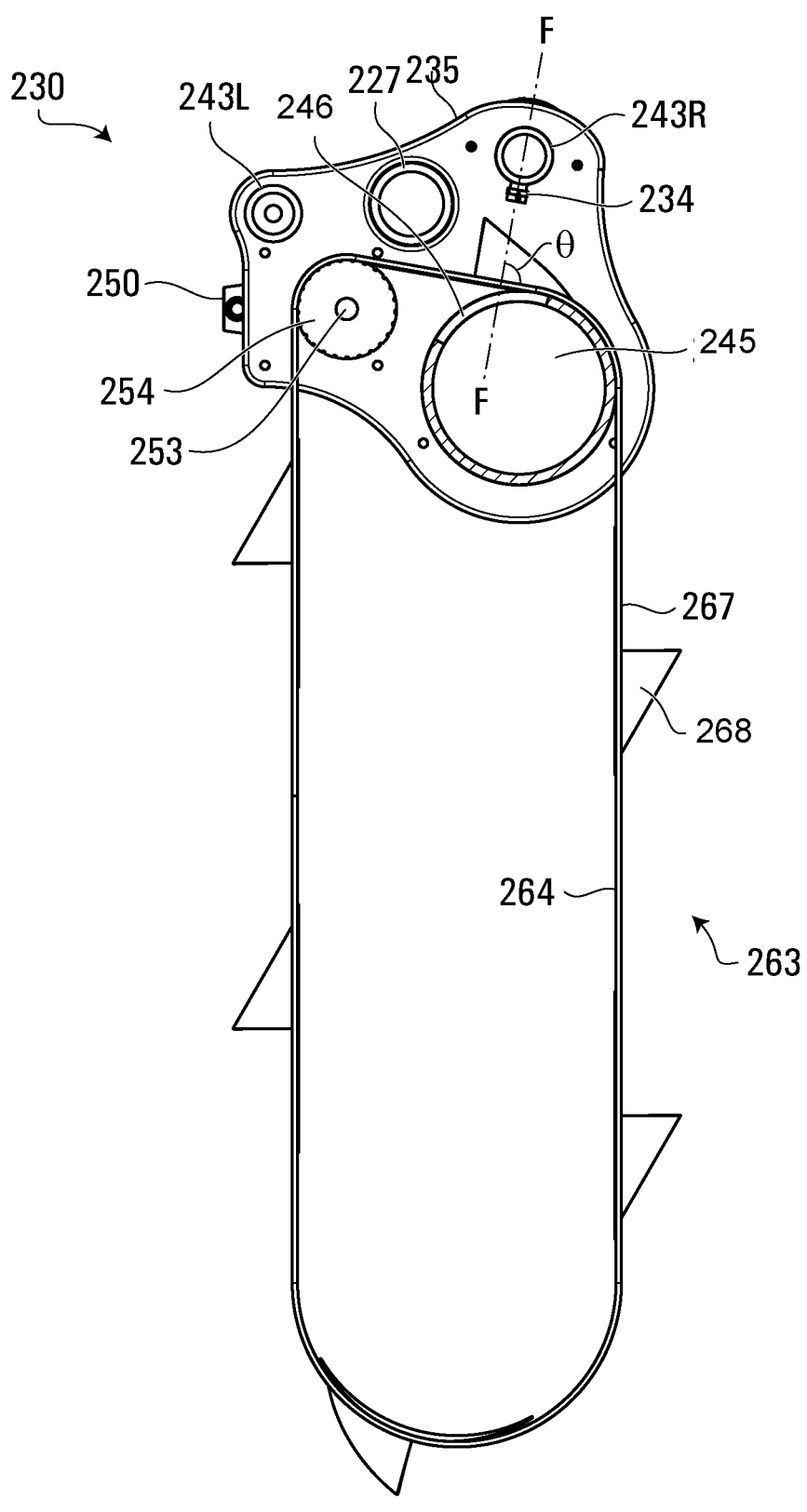
FIG. 20 depicts a second side view of the FIG. 15 apparatus and FIG. 18 filter body.

Once removal apparatus 230 has been assembled and rendered operational, it may be continuously or intermittently operated with controller 180 so that filter body 263 is rotated a rate of 30-50 inches per minute. For example, removal apparatus 30 may be operated intermittently so that each pocket 238 may lift clumps of floating particles (e.g., floating uneaten plankton food and dead plankton) out of culture medium 1, and one or more nozzles 234 may be utilized to remove any portions of the floating particles that become stuck in openings 272 of pockets 268 while lifting. As shown in FIGS. 17 and 20, for example, removal apparatus 230 may be operated to cause movements of each pocket 268 between: (i) a lift position, in which backing portion 268B of is generally perpendicular with top surface 2; (ii) a dump position, in which backing portion 268B is generally parallel with top surface 2 and positioned vertically relative to conduit 245 and input opening 246; and (iii) a removal position, in which protruding portion 268P and backing portion 268B of pocket 268 are positioned under one or more nozzles 234. As shown in FIG. 3, for example, drive element 232 may cause electric motor 250 to rotate gears 254 and 256 responsive to control signals 185 from controller 180, thereby causing gears 254, 256 to rotate filter body 263 so that each pocket 268 is moved between the lift, dump, and removal positions responsive to controller 180.

Put another way, when actuated by controller 180, removal apparatus 230 may rotate filter body 263 in a counterclockwise direction (from viewpoint of FIG. 13) to lift pockets 268 out of culture medium 1 along with the captured particles. A first portion of the lifted particles may fall into input opening 246 of conduit 245 with gravity forces once the filters are positioned over input opening 246. One or more nozzles 334 may spray the removal fluid onto the filter body as it moves across the opening, moving a second portion of the lifted particles away from the filters and into the conduit and generating an effluent flow that is directed away from culture medium 1 in culture tank 220 with the conduit.

The lift position may be utilized to maximize the ability of pocket 268 to lift particles out of culture medium 1 by keeping its 3D filtering shape and scooping portion in an upright position while being moved through culture medium 1 in a generally vertical direction. The dump position may be utilized to cause a first portion of the lifted particles to fall into conduit 45 through openings 272 of pockets 268 with gravity forces. As shown in FIG. 20, for example, each pocket 268 may be deformed by exterior surfaces of outlet post 238, such as the edges of input opening 246, before being positioned over input opening 246 of conduit 245, helping to separate the first portion from pocket 268 by slightly deforming openings 272.

A second portion of the lifted particles may cling to pocket 268 and/or become lodged in its openings 272, making them difficult or impossible to remove with gravity forces. The removal position may be utilized to direct the second portion of the lifted particles into conduit 245 through input opening 246 with impact forces applied by the removal fluid output from one or more nozzles 234. As shown in FIG. 21, for example, filter body 263 may be rotated until pocket 268 is inverted over conduit 245 and input opening 246 so that its backing portion 268B intersects flow path F-F of one or more nozzles 234 at an intersecting angle θ. The removal fluid may be directed along flow path F-F in order to apply impact forces to protruding portion 268P and backing portion 268B at a pressure sufficient to push the second portion of the lifted particles through openings 271 and into conduit 245 through opening 246. The removal fluid may pass across protruding portion 268P and backing portion 268B at a similar intersecting angle θ when filter body 263 is rotated around conduit 245 to dislodge the particles from openings 272 with the impact forces applied by the removal fluid.

Treatment System 340

Similar to treatment system 140, treatment system 340 may be operable to maintain the plankton population in culture medium 1 by removing toxins from and/or adding oxygen to culture medium 1. As before, the nutrients may comprise oxygen and/or other aquaculture supplements; and the toxins may comprise ammonia, nitrogen, and organic wastes.

As shown in FIG. 14, for example, treatment system 340 may be operated to maintain the plankton population by performing a processing method comprising: (i) removing particles from culture medium 1 (e.g., with removal apparatus 130 or other means); (ii) outputting a filtered flow from a filtered portion of culture medium 1 (e.g., with filtration apparatus 80 or other means); (iii) converting the filtered flow in to the processed flow by (a) removing toxins from the filtered flow, and (b) adding oxygen to the filtered flow; and (iv) inputting the processed flow to culture medium 1.

Various elements of treatment system 340 may be adapted to maintain the viability of culture medium 1 according to this method.

As shown in FIG. 14, for example, treatment system 340 may comprise a first loop 341 and a second loop 342 that are switchable between different operating modes with controller 180.

First loop 341 may comprise a biofilter tank 343, a manifold 344, a line 345, a pump 346, and a protein skimmer 347. Biofilter tank 343 of treatment system 340 may be similar to biofilter tank 157 of treatment system 140. As shown in FIG. 14, for example, biofilter tank 343 may input the filtered flow of culture medium 1 output from filtration device 80; and be sized (e.g., at approximately 1,000 L) to generate a volume of treated culture medium 1. In keeping with above, biofilter tank 343 may be shaped similar to biofilter tank 157, and may similarly comprise bioballs, bio-media, carrier materials, and/or any similar structures comprising surface areas for housing colonies of nitrifying bacteria when submerged in the volume of treated culture medium 1 stored in tank 343. In this regard, biofilter tank 343, like biofilter tank 157, also may be operable as a 'Moving Bed Biofilm Reactor.'

Manifold 344 may comprise conduits for directing a flow of the volume of treated culture medium 1 into either line 345 of first loop 341 or a line 355 of second loop 342. As shown in FIG. 15, the flow moves from biofilter tank 343, into manifold 344, and then into line 345, where the flow will be pressurized by pump 346 for entry into protein skimmer 347 before being recirculated back into tank 343 with an outlet of line 345. Controller 180 may cause pump 346 to operate continuously so as to continuously improve the volume of treated culture medium 1 in biofilter tank 343. In keeping with above, pump 346 may be a centrifugal pump (e.g., an Iwaki MD-70RLTZ) that pressurizes the flow of treated culture medium 1 before it is input to protein skimmer 347 (e.g., an RK2 5AC protein fractionator), which may comprise a fluid column that removes organic wastes from the now pressurized flow of culture medium 1 output from pump 346. An output portion of line 345 may direct flows from protein skimmer 346 back into biofilter tank 343.

As shown in FIG. 14, for example, biofilter tank 343 also may comprise a water supply line 348, a flow meter 349, an actuated valve 350, and an overflow drain 351. Actuated valve 348 may be operable with controller 180 and flow meter 349 to input a flow of water into biofilter tank 343 if the volume of culture medium 1 therein drops below a certain level. Conversely, overflow drain 350 may be operable to output a flow of culture medium 1 from tank 343 when the volume of medium 1 therein exceeds a maximum level.

Second loop 342 may comprise a line 355, a pump 356, a switch 357, a biocarbonate source 361, a food source 362, and a line 363. As shown in FIG. 14, for example, manifold 344 may direct a flow of the additional volume of culture medium 1 in biofilter tank 343 into line 355. Pump 356 may be a centrifugal pump (e.g., an Iwaki WMD20RLT-115) that pressurizes the flow of culture medium 1 in line 355 to a desired pressure, directing it into culture tank 220. Pump 356 may cause a low pressurization as it discharges to atmosphere inside tank 343. For example, the flow rate culture medium 1 output from line 355 may be approximately ⁻10 liters per minute. Switch 357 may be operable with controller 180 to control pump 356.

Biocarbonate source 361 may be operable with controller 180 to maintain a pH level of the volume of culture medium 1 contained in culture tank 220. For example, a pH sensor may be located in tank 220 and operable with controller 180 to cause biocarbonate source 361 to dispense amounts of biocarbonate as needed to maintain the pH level. Food source 362 may be operable with controller 180 to dispense food into the volume of culture medium 1 contained in culture tank 220. For example, a food density sensor (e.g., an optical camera) may be located in tank 220 and operable with controller 180 to cause food source 362 to dispense amounts of food as needed to maintain a minimum level of food density in culture tank 220. As shown in FIG. 14, for example, the filtered flow from filtration device 80 may be output to line 363, directed into pump 346 through line 345, and pressurized before being input to protein skimmer 347 and output to biofilter tank 343 as described above.

Treatment system 340 also may comprise an oxygen supply line 358, an air supply line 359, and a diffuser 360. In contrast to above, the volume of culture medium 1 in culture tank 220 may be supplied with continuous flows of oxygen from oxygen supply line 358 and air from an air supply line 359. As shown in FIG. 14, for example, oxygen supply line 358 may be coupled to a source of oxygen (e.g., an oxygen tank) and operable with controller 180 to direct a continuous flow of oxygen into the volume of culture medium 1 in culture tank 220; and air supply line 359 may be coupled to a source of air (e.g., an air compressor tank) and operable with controller 180 to direct a continuous flow of air into the volume of medium 1 contained in tank 220. As shown in FIG. 22, for example, diffuser 360 may comprise an "air stone" or similar device that diffuses the oxygen and air into the culture medium 1 in tank 220. As shown in FIG. 22, for example, diffuser 360 may be located inside of tank 220 and positioned to circulate the volume of culture medium 1. The circulation may be directed toward one or both of filtration apparatus 80 and removal apparatus 230. Diffuser 360 may be operable to diffuse the air and oxygen in a first direction toward apparatus 80 (e.g., shown with upward arrows) that causes particles in the culture medium to move in a second direction toward apparatus 280 (e.g., shown with downward arrows), thereby guiding the particles toward filter body 263 and into pockets 268. As shown in FIG. 22, for example, diffuser 360 may be placed on the left side of culture tank 220, beneath filtration apparatus 80, to help induce a convective flow that rises under filtration apparatus 80 and drops on the right side at removal apparatus 230. The convective flow causes culture medium 1, and thus particles, to move down through filters of a filter body of removal apparatus 280, allowing the particles to be captured with the filters. The convective flow also may keep particles suspended in culture medium.

Treatment system 340 may thus be switched into at least two different modes, including: (i) a feeding mode; and (ii) a cleaning mode. As shown in FIGS. 13 and 14, for example, treatment system 340 may be switched into the feeding mode with controller 180 by causing switch 357 to disable pump 356 in order to stop the flow of treated culture medium 1 into culture tank 220.

Oxygen supply line 358 and air supply line 359 may operate continuously when treatment system 340 is in the cleaning mode and/or the feeding mode. Removal apparatus 230 and/or filtration apparatus 80 may be operated intermittently and/or not at all when system 340 is in the feeding mode. Apparatus 230 and/or 80 may operate independently of the mode of system 340. As described herein, culture tank 220 may hold a population of plankton (e.g., rotifers) and feeding may take place inside tank 220 when controller 180 causes food source 361 to release food into tank 220. The plankton population may consume amounts of the food and oxygen in the volume of culture medium 1 in tank 220, and release amounts of carbon dioxide and nitrogenous waste products back into the volume of culture medium 1 in culture tank 220. Stopping the flow of treated culture medium 1 into tank 220 during feeding prevents the food from being diluted and/or removed, making the feeding mode of treatment system 340 a useful tool for reducing the operating costs of system 210.

When the feeding cycle is completed (e.g., after a predetermined amount of time), treatment system 340 may be switched into the cleaning mode with controller 180 by causing switch 357 to activate pump 356 in order to direct a flow of processed culture medium 1 from biofilter tank 343 into culture tank 220 through line 355. Pump 346 may be operated continuously to ensure that a steady supply of treated culture medium 1 is ready and available in biofilter tank 343, and so that the culture medium 1 inside of biofilter tank 343 is continuously improved. The treated culture medium 1 input to culture tank 220 from line 355 may cause the fluid level in tank 220 to rise until it reaches an outlet post of filtration device 280 that route the flow into line 355 for addition to culture tank 220 via pump 346 and line 345.

When treatment system 340 is in the cleaning mode, the plankton population may have less food available, causing their oxygen consumption to drop, allowing the oxygen levels in tank 220 to rise due to the continuous addition of oxygen and air from supply lines 361 and 362. The resulting dilution of waste products due to the fluid exchange with biofilter tank 343, combined with the waste removed by operation of removal apparatus 230, may increase the quality of culture medium 1, thereby improving the health of the plankton population. At the end of the cleaning cycle, the quality of culture medium 1 may be greatly improved. As which point, treatment system 340 may again be switched into the feeding mode with controller 180 by causing switch 357 to disable pump 356 in order to stop the flow of culture medium 1 into culture tank 220.

As described herein, system 10, system 210, and any obvious variations thereof, may function as a semi-automated, partially closed loop bioreactor that is uniquely configured for maintaining healthy plankton populations. Compared to industry standard systems, the described systems may use less water, food, and labor hours while producing a biologically superior product with lower counts of pathogenic bacteria and contaminating microorganisms, such as ciliates.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A method for maintaining plankton in a culture medium, the method comprising:
    moving a first area of a filter engaged with a filter body into the culture medium, the filter body having an interior cavity, the filter being adapted to keep the plankton and particles in the culture medium out of the interior cavity while permitting the culture medium to pass into the interior cavity;
    generating a filtered portion of the culture medium by passing a volume of the culture medium through the first area and into the interior cavity;

outputting a filtered flow from a location in the interior cavity;
    rotating the filter body to
        remove the first area from the culture medium along with a number of the plankton and the particles attached to the first area, and
        move a second area of the filter into the culture medium;
    directing a cleaning fluid toward the filter body to move the number of the plankton and the particles off the first area and into the culture medium;
    converting the filtered flow into a processed flow by removing toxins from the filtered flow with a treatment system;
    inputting the processed flow to the culture medium; and
    continuously adding oxygen to the culture medium.

2. The method of claim 1, comprising:
    further rotating the filter body to
        remove the second area from the culture medium along with a second number of the plankton and the particles attached to the second area, and
        move a third area of the filter into the culture medium; and
    directing the cleaning fluid toward the filter body to move the second number of the plankton and the particles off the second area and into the culture medium.

3. The method of claim 2, comprising intermittently repeating the rotating and directing steps for each different area of the filter.

4. The method of claim 1, comprising performing the directing step while performing the rotating step.

5. The method of claim 1, wherein the directing step comprises one or both of:
    directing a first amount of the cleaning fluid toward an interior surface of the filter body from a location in the interior cavity; and
    directing a second amount of the cleaning fluid toward an exterior surface of the filter body from a location outside the interior cavity.

6. The method of claim 1, wherein:
    the first and second areas of the filter comprise openings sized to keep the plankton and the particles out of the interior cavity while permitting the culture medium to pass into the interior cavity;
    a portion of the number of the plankton and the particles are attached in the openings of the first area; and
    the method comprises directing the cleaning fluid toward the filter body to push the portion of the number of the plankton and the particles out of the openings.

7. The method of claim 1, wherein the culture medium is stored in a tank, the filter body is rotatable in a frame, and the method comprises engaging the frame with the tank so that only one different area of the filter is submerged in the culture medium at a time to limit biofouling of the filter and the filter body.

8. The method of claim 7, wherein method comprises one or both of:
    removing the filter body from the frame; and
    removing the filter from the filter body.

9. An apparatus for maintaining plankton in a culture medium, the apparatus comprising:
    a filter body having an interior cavity;
    a filter engaged with the filter body and adapted to keep the plankton and particles in the culture medium out of the interior cavity while permitting a volume of the culture medium to pass into the interior cavity through a first area of the filter;

an outlet adapted to output a filtered flow from a location in the interior cavity to a treatment system adapted to convert the filtered flow into a processed flow by removing toxins from the filtered flow;

a drive element adapted to rotate the filter body to remove the first area from the culture medium along with a number of the plankton and the particles attached to the first area, and move a second area of the second filter into the culture medium;

one or more nozzles adapted to direct a cleaning fluid toward the filter body to move the number of the plankton and the particles off the first area and into the culture medium;

an inlet adapted to input the processed flow to the culture medium; and an oxygen source adapted to continuously add oxygen to the culture medium.

10. The apparatus of claim 9, wherein:

the drive element is adapted to further rotate the filter body to remove the second area from the culture medium along with a second number of the plankton and the particles attached to the second area, and move a third area of the filter into the culture medium; and the one or more nozzles are adapted to direct the cleaning fluid toward the filter body to move the second number of the plankton and the particles off the second area and into the culture medium.

11. The apparatus of claim 9, wherein the drive element is adapted to intermittently rotate the filter body.

12. The apparatus of claim 9, wherein the one or more nozzles are adapted to direct the cleaning fluid when the drive element is rotating the filter body.

13. The apparatus of claim 9, wherein the one or more nozzles are adapted to direct one or both of:

a first amount of the cleaning fluid toward an interior surface of the filter body from a location in the interior cavity; and a second amount of the cleaning fluid toward an exterior of the filter body from a location outside the interior cavity.

14. The apparatus of claim 9, wherein the first and second areas of the filter comprise openings sized to keep the plankton and the particles out of the interior cavity while permitting the culture medium to pass into the interior cavity;

a portion of the number of the plankton and the particles are attached in the openings of the first area; and the one or more nozzles are adapted to direct the cleaning fluid toward the filter body to push the portion of the number of the plankton and the particles out of the openings.

15. The apparatus of claim 9, wherein the culture medium is stored in a tank, the filter body is rotatable in a frame, and the frame is engageable with the tank so that only one different area of the filter is submerged in the culture medium at a time to limit biofouling of the filter and the filter body.

16. The apparatus of claim 15, wherein at least one of:

the filter body is removable from the frame; and the filter is removable from the filter body.

17. A system for maintaining plankton in a culture medium contained in a culture tank, the system comprising:

a first apparatus adapted to remove particles from the culture medium in the culture tank;

a second apparatus comprising the apparatus of claim 9; and the treatment system, wherein the treatment system is operable to convert the filtered flow into a treated culture medium and comprises:

a first loop operable to add food to the culture tank, and a second loop operable to add the treated culture medium into the culture tank.

18. The system of claim 17, wherein the oxygen source comprises a diffuser operable to diffuse a flow of the air and oxygen in a first direction toward the second apparatus and the flow causes a portion of the particles in the culture medium to move in a second direction toward the first apparatus.

19. The system of claim 17, wherein the treatment system comprises a treatment loop operable to remove toxins from the filtered flow.

20. The system of claim 19, wherein the treatment loop is operable continuously and the first and second loops are operable intermittently.

* * * * *